(12) United States Patent
Nagy et al.

(10) Patent No.: US 11,337,924 B2
(45) Date of Patent: *May 24, 2022

(54) TARGETED POLYMERIZED NANOPARTICLES FOR CANCER TREATMENT

(71) Applicants: Children's Hospital Los Angeles, Los Angeles, CA (US); Nanovalent Pharmaceuticals, Inc., Bozeman, MT (US)

(72) Inventors: Jon O. Nagy, Bozeman, MT (US); Tim Triche, Los Angeles, CA (US); Hyung-Gyoo Kang, Buena Park, CA (US)

(73) Assignees: Children's Hospital Los Angeles, Los Angeles, CA (US); Nanovalent Pharmaceuticals, Inc., Bozeman, MT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/444,842

(22) Filed: Jun. 18, 2019

(65) Prior Publication Data

US 2019/0365650 A1     Dec. 5, 2019

Related U.S. Application Data

(63) Continuation of application No. 15/301,020, filed as application No. PCT/US2015/023943 on Apr. 1, 2015, now Pat. No. 10,369,104.
(Continued)

(51) Int. Cl.
*A61K 9/127*     (2006.01)
*A61K 45/06*     (2006.01)
(Continued)

(52) U.S. Cl.
CPC .......... *A61K 9/1273* (2013.01); *A61K 9/1271* (2013.01); *A61K 9/51* (2013.01);
(Continued)

(58) Field of Classification Search
CPC .................................................... A61K 9/1273
See application file for complete search history.

(56) References Cited

U.S. PATENT DOCUMENTS 6,183,772 B1    2/2001   Charych et al.
9,956,176 B2 *  5/2018   Nagy .................. A61K 9/0043
(Continued)

FOREIGN PATENT DOCUMENTS

AU     2015240766 A1    10/2016
CA        2943365 A1    10/2015
(Continued)

OTHER PUBLICATIONS

N Federman et al. "Enhanced Growth Inhibition of Osteosarcoma by Cytotoxic Polymerized Liposomal Nanoparticles Targeting the Alcam Cell Surface Receptor." Sarcoma, vol. 2012, Article ID 126906, pp. 1-11, published in 2012. (Year: 2012).*
(Continued)

*Primary Examiner* — Isaac Shomer
(74) *Attorney, Agent, or Firm* — Nixon Peabody LLP

(57) ABSTRACT

The invention relates to a novel drug delivery vehicle. Various embodiments of the invention provide a hybrid polymerized liposomal nanoparticle comprising both polymerizable lipids and non-polymerizable lipids. Therapeutic agents can be loaded into the polymerized liposomal nanoparticle and targeting agents can be conjugated to the surface of the polymerized liposomal nanoparticle. Also described in the invention are methods, compositions and kits that utilize the hybrid polymerized liposomal nanoparticle to treat disease conditions such as various cancers.

15 Claims, 13 Drawing Sheets

Related U.S. Application Data

(60) Provisional application No. 61/973,760, filed on Apr. 1, 2014.

(51) Int. Cl.

| | | |
|---|---|---|
| *A61K 9/51* | (2006.01) | |
| *A61K 31/136* | (2006.01) | |
| *A61K 31/337* | (2006.01) | |
| *A61K 31/407* | (2006.01) | |
| *A61K 31/4745* | (2006.01) | |
| *A61K 31/475* | (2006.01) | |
| *A61K 31/573* | (2006.01) | |
| *A61K 31/704* | (2006.01) | |
| *A61K 31/7068* | (2006.01) | |
| *A61K 31/713* | (2006.01) | |
| *A61K 33/243* | (2019.01) | |

(52) U.S. Cl.
 CPC .......... *A61K 31/136* (2013.01); *A61K 31/337* (2013.01); *A61K 31/407* (2013.01); *A61K 31/475* (2013.01); *A61K 31/4745* (2013.01); *A61K 31/573* (2013.01); *A61K 31/704* (2013.01); *A61K 31/7068* (2013.01); *A61K 31/713* (2013.01); *A61K 45/06* (2013.01); *A61K 33/243* (2019.01); *Y10S 977/773* (2013.01); *Y10S 977/906* (2013.01); *Y10S 977/907* (2013.01)

(56) References Cited

U.S. PATENT DOCUMENTS

| | | | | |
|---|---|---|---|---|
| 10,369,104 | B2* | 8/2019 | Nagy | .................. A61K 31/713 |
| 2004/0253184 | A1* | 12/2004 | Li | ..................... A61K 49/1812 |
| | | | | 424/9.363 |
| 2008/0226619 | A1* | 9/2008 | Rubinstein | ......... C07K 16/3092 |
| | | | | 424/130.1 |
| 2011/0319472 | A1 | 12/2011 | Mackintosh Ginel | |
| 2013/0129635 | A1 | 5/2013 | Nagy et al. | |
| 2013/0273146 | A1 | 10/2013 | Maurer et al. | |
| 2013/0337067 | A1 | 12/2013 | Prakash | |
| 2015/0182640 | A1 | 7/2015 | Sim et al. | |
| 2017/0020816 | A1 | 1/2017 | Nagy et al. | |
| 2017/0143630 | A1 | 5/2017 | Nagy et al. | |

FOREIGN PATENT DOCUMENTS

| | | | |
|---|---|---|---|
| EP | 3129062 | A2 | 2/2017 |
| JP | 07-173079 | A | 7/1995 |
| JP | 2017512840 | A | 5/2017 |
| WO | WO 2009/102782 | A2 | 8/2009 |
| WO | WO 2009/120247 | A2 | 10/2009 |
| WO | WO 2011/149985 | A1 | 12/2011 |
| WO | WO-2011149985 | A1 * | 12/2011 .......... A61K 49/223 |
| WO | WO 2012/155021 | A1 | 11/2012 |
| WO | WO-2012155021 | A1 * | 11/2012 .......... A61K 9/1272 |
| WO | WO 2013/155493 | A1 | 10/2013 |
| WO | WO 2014/007517 | A1 | 1/2014 |
| WO | WO 2015/153805 | A2 | 10/2015 |

OTHER PUBLICATIONS

Hye Choi and Joon Sig Choi. "Characteristics of PEGylated Polydiacetylene Liposome and its Inclusion Complex Formation with α-Cyclodextrin." Bulletin of the Korean Chemical Society, vol. 34, No. 10, 2013, pp. 3083-3087. (Year: 2013).*

Hye Choi, Yun Mi Bae, Gwang Sig Yu, Kang Moo Huh*, and Joon Sig Choi. "Synthesis of Poly(ethylene glycol)-Polydiacetylene Conjugates and Their Micellar and Chromic Characteristics." Journal of Nanoscience and Nanotechnology vol. 8, 2008, pp. 5104-5108. (Year: 2008).*

Ann M. Bode and Zigang Dong. "Cancer prevention research—then and now." Nature Reviews, vol. 9, Jul. 2009, pp. 508-516. (Year: 2009).*

Yoonjee Park, Adam C. Luce, Ragnhild D. Whitaker, Bhumica Amin, Mario Cabodi, Rikkert J. Nap, Igai Szleifer, Robin O. Cleveland, Jon O. Nagy, and Joyce Y. Wong "Tunable Diacetylene Polymerized Shell Microbubbles as Ultrasound Contrast Agents." Langmuir, vol. 28, 2012, pp. 3766-3772. (Year: 2012).*

Steven P. Wrenn, Stephen M. Dicker, Eleanor F. Small, Nily R. Dan, Michal Mleczko, Georg Schmitz, and Peter A. Lewin. "Bursting Bubbles and Bilayers." Theranostics, vol. 2(12), 2012, pp. 1140-1159. (Year: 2012).*

PCT/US2015/023943 Int'l Search Report and Written Opinion dated Oct. 7, 2015.

PCT/US2015/023943 Int'l Preliminary Report on Patentability dated Oct. 4, 2016.

EP 15772301 Extended European Search Report dated Oct. 26, 2017.

Federman et al., Enhanced Growth Inhibition of Osteosarcoma by Cytotoxic Polymerized Liposomal Nanoparticles Targeting the Alcam Cell Surface Receptor, Sarcoma, 2012, vol. 2012, 11 pages.

Park et al., Tunable Diacetylene Polymerized Shell Microbubbles as Ultrasound Contrast Agents, Langmuir, 2012, vol. 28, pp. 3766-3772.

Yavlovich et al., Design of Liposomes Containing Photopolymerizable Phospholipids for Triggered Release of Contents, J. Therm. Anal. Calorim. 2009, 98(1), pp. 97-104.

* cited by examiner

FIG. 2
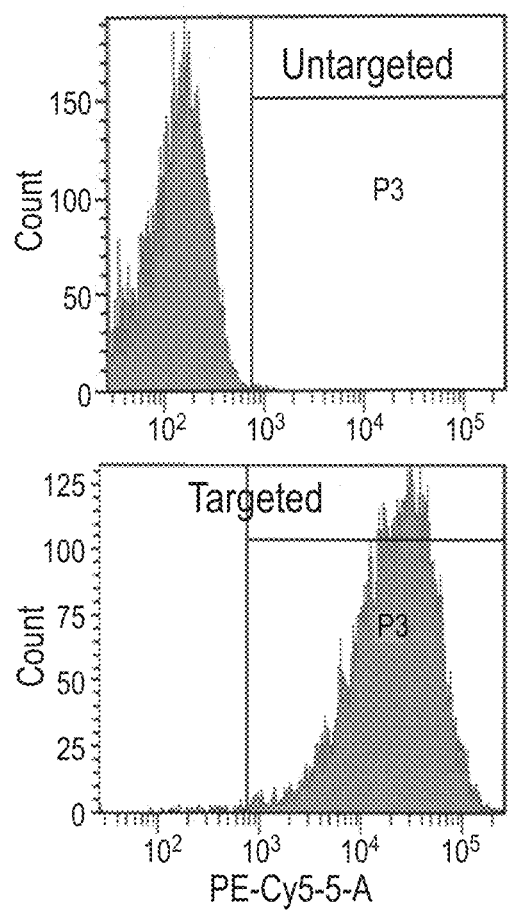
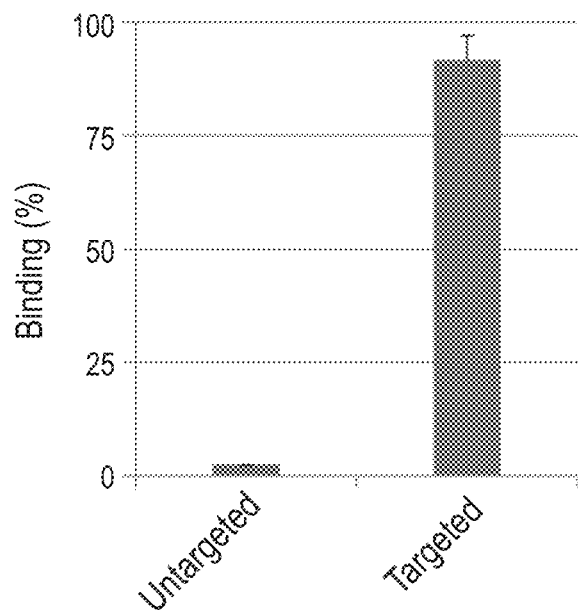
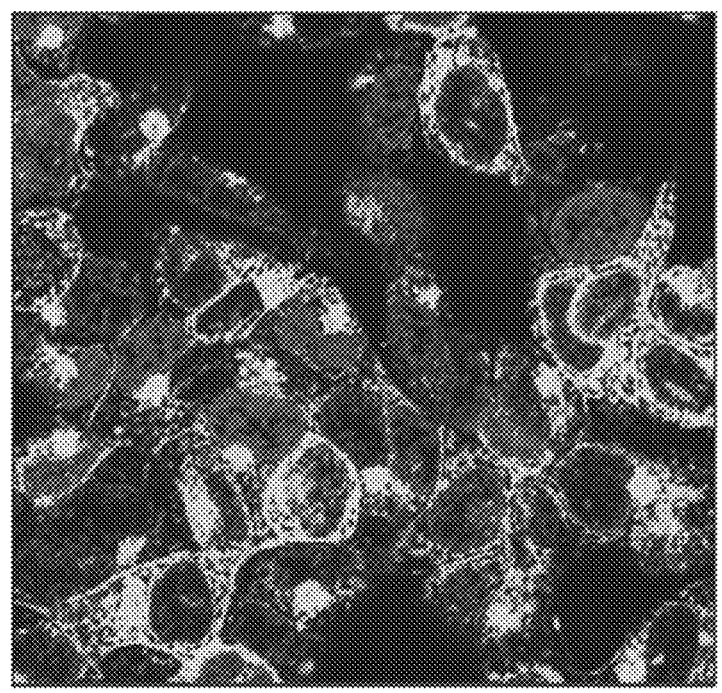

FIG. 5
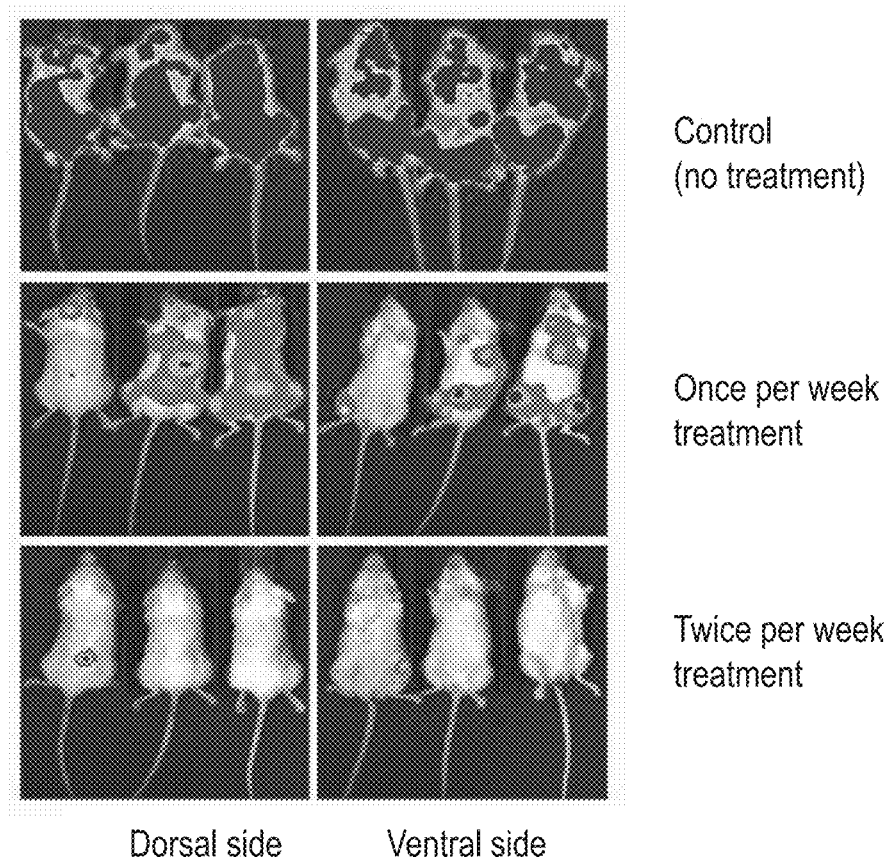
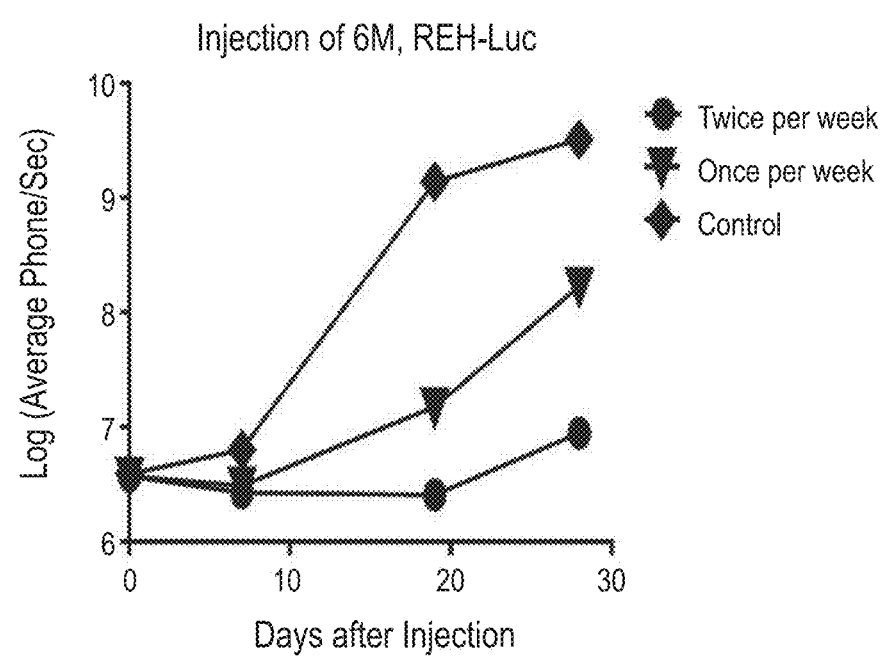

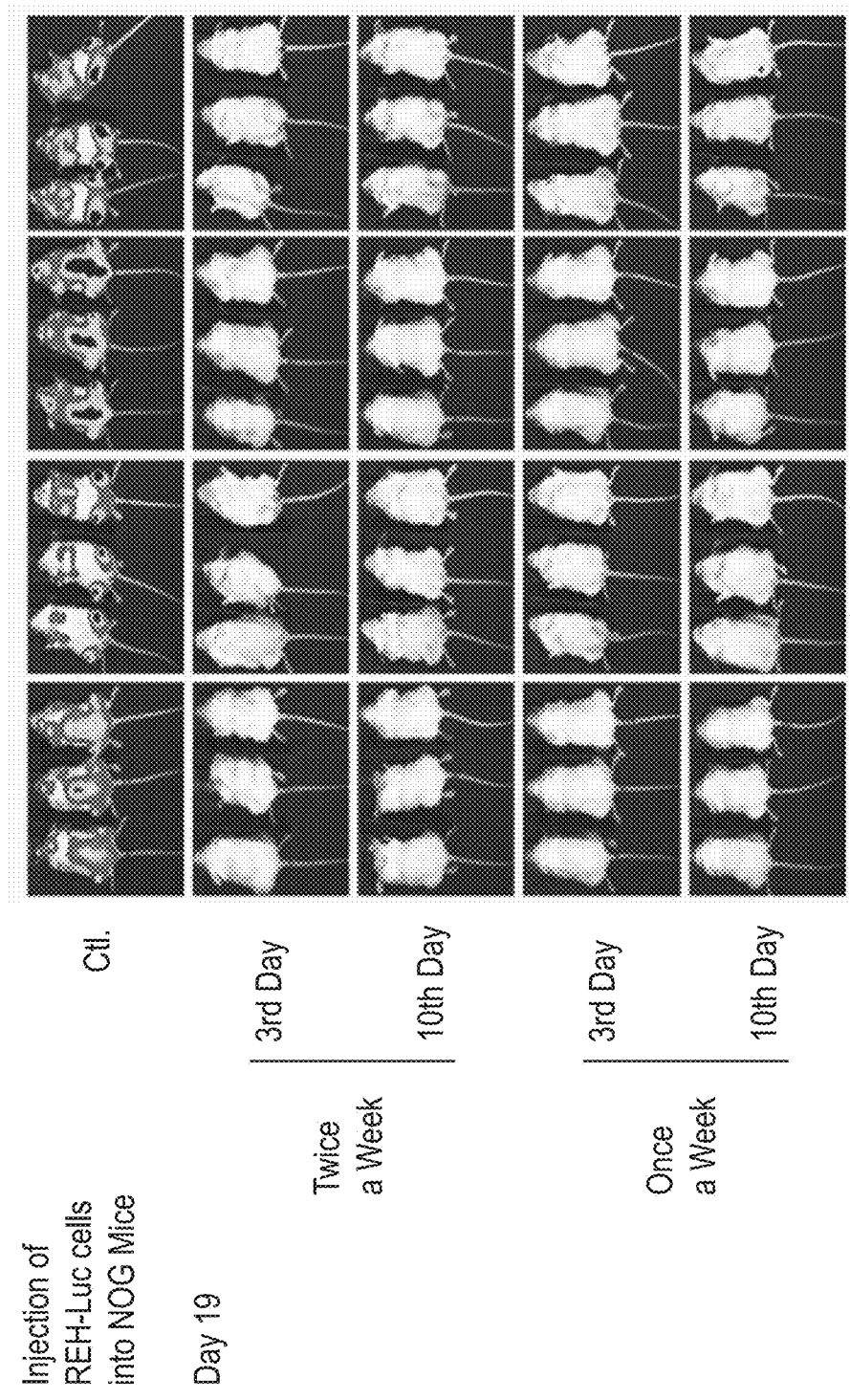

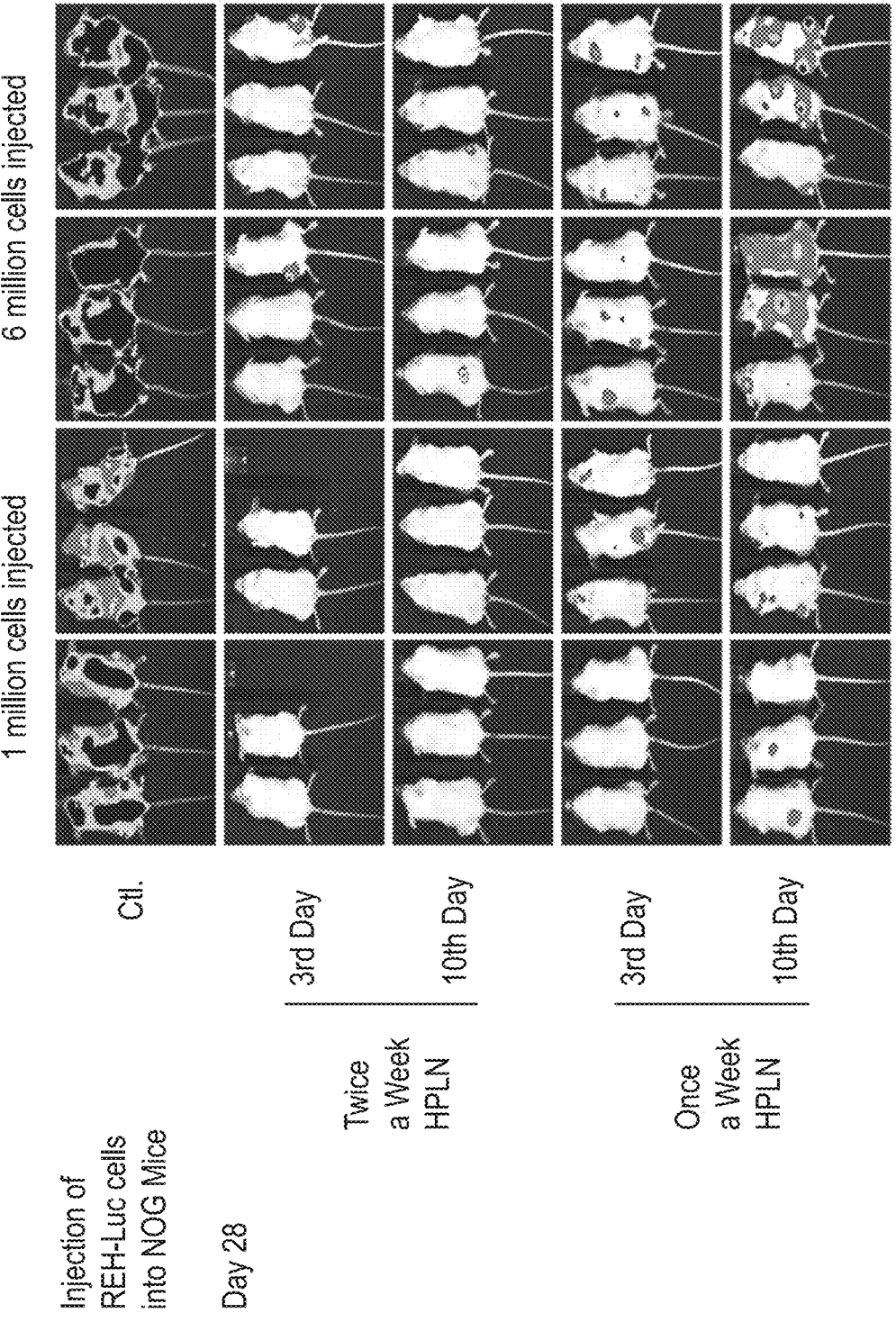

Untreated　　　　　　　　　Targeted HPLN

TARGETED POLYMERIZED NANOPARTICLES FOR CANCER TREATMENT

CROSS-REFERENCE TO RELATED APPLICATIONS

This application is a continuation of U.S. application Ser. No. 15/301,020 filed Sep. 30, 2016, which is a National Phase of International Application No. PCT/US2015/023943 filed Apr. 1, 2015, which designated the U.S. and that International Application was published under PCT Article 21(2) in English, which claims priority under 35 U.S.C. § 119(e) to U.S. Provisional Application No. 61/973,760 filed Apr. 1, 2014, the contents of each of which are incorporated herein by reference in their entirety.

STATEMENT REGARDING FEDERALLY-SPONSORED RESEARCH

This invention was made with government support under Grant No. IIP-1143342 awarded by the National Science Foundation. The government has certain rights in the invention.

FIELD OF THE INVENTION

The invention relates to compositions, methods and kits for treating a condition with a targeted hybrid polymerized liposomal nanoparticle as a novel drug delivery vehicle. The condition includes but is not limited to various cancers. The hybrid polymerized liposomal nanoparticle is targeted to a cancer cell, becomes internalized in the cancer cell and releases the encapsulated drug to damage/destroy the cancer cell.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Worldwide, an estimated 350,000 people are diagnosed with leukemia each year, with approximately 257,000 deaths annually (International Agency for Research on Cancer). In the U.S. alone, an estimated 274,930 people are living with leukemia, with about 90 percent of all leukemia diagnosed in adults (World Health Organization). In 2012, 47,150 new patients were diagnosed, with only about 50 percent expected to survive (American Cancer Society). While conventional frontline therapies are effective in many cases, it is obvious from the low survival rate of leukemia patients that there is an imperative for improvement.

Leukemia is very expensive to treat, and many patients are unable to afford treatment. Most patients with leukemia are treated with chemotherapy (Ohio State University's Comprehensive Cancer Center). Just one chemotherapy treatment can cost $150,000, usually with several treatments needed. An optional treatment, bone-marrow transplants are known to cost $250,000 or more (Edgar Law Firm, Santa Rosa, Calif.). The National Cancer Institute's Cancer Trends Progress Report: 2011-2012 update estimates that $5.4 billion is spent in the United States each year on leukemia treatment, or more than $114,500 for each of the 47,150 patients diagnosed in 2012.

Herein, we provide a drug delivery system, in which hybrid polymerized liposomal nanoparticles (HPLNs) are utilized to encapsulate cancer drugs and deliver the cancer drugs to the cancer cells. The described delivery system can be used for encapsulating virtually any drug of interest and targeting to any tissue for which there is a known unique or specific cell marker. Therefore this invention provides a very versatile platform technology.

The HPLNs described herein offer a major advantage over many other types of delivery particle substances by employing a unique type of nanoparticle material that is both biocompatible and enhances the bioavailability of the drugs encapsulated within. In addition, the technology is customized by adjusting the particle properties so that a high amount of the drug agent is contained within, and actually solidified into a crystal. Still another differentiating feature is a customization process that appends a tumor-targeting molecule to the surface of the particle, thus improving the particles' selectivity in accessing tumorous cells while avoiding healthy tissues.

Through the use of drugs encapsulated in HPLNs, physicians treating cancer patients may see a significant increase in the therapeutic window of existing cancer chemotherapeutic substances by minimizing dose-related toxicity on non-cancerous cells. For these patients, the HPLNs described herein hold the promise of more effective treatment, accomplished through several significant attributes: a) shorter treatment time, b) fewer hospital visits, c) less damage to normal tissues, d) more rapid recovery, and e) greater chance of survival.

SUMMARY OF THE INVENTION

Various embodiments of the present invention provide hybrid polymerized liposomal nanoparticle (HPLN). The HPLN may comprise or consist of consist of a polymerizable lipid, wherein the polymerizable lipid comprises at least one PEGylated polymerizable lipid having a PEG polymer chain, and a non-polymerizable lipid. In an embodiment, the PEGylated polymerizable lipid is m-PEG2000-PCDA.

Various embodiments of the present invention provide a HPLN. The HPLN may comprise or consist of a polymerizable lipid (about 15-40 mol %), wherein the polymerizable lipid comprises at least one PEGylated polymerizable lipid having a PEG polymer chain, and non-polymerizable lipids. In some embodiments, the non-polymerizable lipids comprise a zwitterionically charged lipid (at least about 10 mol %), a neutrally charged molecule (about 20-45 mol %), a negatively charged lipid (about 1-15 mol %) and/or combinations thereof. In an embodiment, the PEGylated polymerizable lipid is m-PEG2000-PCDA.

In some embodiments, the polymerizable lipid comprises at least one polymerizable lipid having no PEG polymer chain (only a single ethylene glycol unit "PEG1"), including but not limited to, h-PEG1-PCDA, sulfo-PEG1-PCDA, m-PEG1-PCDA, and mal-PEG1-PCDA.

In various embodiments, the PEGylated polymerizable lipid having a PEG polymer chain is about 0.1-1, 1-5, 5-10, 10-15, 1-15, 15-30, or 30-40 mol % of the HPLN. In various embodiments, the PEG polymer chain comprises about 10-150, 10-50, 50-100, or 100-150 PEG units. In various embodiments, the molecular weight of the PEG polymer chain is about 500-5000, 500-2000, or 2000-5000 Da. In various embodiments, the PEGylated polymerizable lipid is selected from the group consisting (PEG)n-10,12-pentacosadiynoic acid (h-(PEG)n-PCDA, sulfo-(PEG)n-PCDA, m-(PEG)n-PCDA, and mal-(PEG)n-PCDA derivatives, wherein n is the number of the PEG units in the PEG polymer chain and is about 10-150, 10-50, 50-100, or 100-150. In various embodiments, the PEGylated polymerizable lipid is selected from the group consisting PEG(mw)-10,12-pentacosadiynoic acid h-PEG(mw)-PCDA, sulfo-PEG(mw)-PCDA, m-PEG(mw)-PCDA, and mal-PEG(mw)-PCDA derivatives, wherein mw is the molecular weight of the PEG polymer chain and is about 500-5000, 500-2000, or 2000-5000 Da. In certain embodiments, the PEGylated polymerizable lipid is PEG2000-10-12-pentacosadiynamide or PEG2000-10-12-pentacosadiynoate. Examples of PEGylated polymerizable lipids include but are not limited to, PEGylated Diyne PC, PEGylated Diyne PE, and PEGylated 10,12-pentacosadiynoic acid (PEG-PCDA) and their functional derivatives and analogs. In some embodiments, the PEGylated polymerizable lipid may comprise a PEGylated polymerizable group attached to a lipid molecule.

In various embodiments, zwitterionically charged lipids include but are not limited to L-α-distearoylphosphatidylcholine, L-α-phosphatidylcholine hydrogenated soy (hydrogenated soy PC), or distearoylphosphatidylcholine (DSPC), 1,2-didecanoyl-sn-glycero-3-phosphocholine (DDPC), 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC) 1,2-diarachidoyl-sn-glycero-3-phosphocholine (DAPC), 1,2-dilignoceroyl-sn-glycero-3-phosphocholine, human serum albumin (HSA).

In various embodiments, neutrally charged molecules include but are not limited to cholesterol, ergosterol, hopanoids, phytosterol, stanol, and sterols, and functional derivatives thereof.

In various embodiments, negatively charged lipids include but are not limited to m-PEG2000-lipid, mal-PEG2000-lipid, (PEG)n-lipid, m-(PEG)n-lipid, mal-(PEG)n-lipid, PEG(mw)-lipid, m-PEG(mw)-lipid, and mal-PEG(mw)-lipid derivatives, where the lipid is DSPE, DMPE, DLPE, DCPE, DAPE or dilignoceroyl-sn-glycero-3-phosphoethanolamine and wherein n is the number of the PEG units in the PEG polymer chain and is about 10-150, 10-50, 50-100, or 100-150 and wherein mw is the molecular weight of the PEG polymer chain and is about 500-5000, 500-2000, or 2000-5000 Da.

In various embodiments, the present invention provides a hybrid polymerized liposomal nanoparticle, comprising about 14 mol % h-PEG1PCDA, about 51 mol % hydrogenated soy PC, about 32 mol % cholesterol, about 2 mol % m-PEG2000-DSPE, and about 1 mol % m-PEG2000-PCDA. In an embodiment, the HPLN further comprises one or more therapeutic agent, as described herein, encapsulated in the HPLN. In an embodiment, the HPLN further comprises one or more antibodies, as described herein, conjugated to the HPLN. In an embodiment, the HPLN comprises one or more therapeutic agents encapsulated in the HPLN and one or more antibodies conjugated to the HPLN.

In various embodiments, the present invention provides a hybrid polymerized liposomal nanoparticle, comprising about 14 mol % h-PEG1PCDA, about 48 mol % hydrogenated soy PC, about 32 mol % cholesterol, about 2 mol % m-PEG2000-DSPE, about 3 mol % mal-PEG2000-DSPE, and about 1 mol % m-PEG2000-PCDA. In an embodiment, the HPLN further comprises one or more therapeutic agent, as described herein, encapsulated in the HPLN. In an embodiment, the HPLN further comprises one or more antibodies, as described herein, conjugated to the HPLN. In an embodiment, the HPLN comprises one or more therapeutic agents encapsulated in the HPLN and one or more antibodies conjugated to the HPLN.

Various embodiments of the present invention provide a method of treating, preventing, reducing the likelihood of having, reducing the severity of and/or slowing the progression of a condition in a subject. The method comprises or consists of providing a hybrid polymerized liposomal nanoparticle described herein and administering a therapeutically effective amount of the hybrid polymerized liposomal nanoparticle to the subject, thereby treating, preventing, reducing the likelihood of having, reducing the severity of and/or slowing the progression of the condition in the subject. In various embodiments, the condition is a cancer. In accordance with the present invention, the hybrid polymerized liposomal nanoparticles further include a therapeutic agent loaded inside the HPLN. Still in accordance with the present invention, the hybrid polymerized liposomal nanoparticles further include a targeting agent, for example on the surface of the HPLN. In some embodiments, the HPLNs include both, a therapeutic agent and a targeting agent.

Various embodiments of the present invention provide a method of treating, preventing the relapse of, reducing the severity of and/or slowing the progression of Ewing sarcoma in a subject. The method comprise or consists of providing a hybrid polymerized liposomal nanoparticle described herein and administering a therapeutically effective amount of the hybrid polymerized liposomal nanoparticle to the subject, thereby treating, preventing the relapse of, reducing the severity of and/or slowing the progression of Ewing sarcoma in the subject. In accordance with the present invention, the hybrid polymerized liposomal nanoparticles further include a therapeutic agent loaded inside the HPLN. Still in accordance with the present invention, the hybrid polymerized liposomal nanoparticles further include a targeting agent, for example on the surface of the HPLN. In some embodiments, the HPLNs include both, a therapeutic agent and a targeting agent.

Various embodiments of the present invention provide a method of treating, preventing the relapse of, reducing the severity of and/or slowing the progression of acute lymphoblastic leukemia (ALL) in a subject. In an embodiment, ALL is childhood ALL. The method comprises or consists of providing a hybrid polymerized liposomal nanoparticle described herein and administering a therapeutically effective amount of the hybrid polymerized liposomal nanoparticle to the subject, thereby treating, preventing the relapse of, reducing the severity of and/or slowing the progression of ALL in the subject. In accordance with the present invention, the hybrid polymerized liposomal nanoparticles further include a therapeutic agent loaded inside the HPLN. Still in accordance with the present invention, the hybrid polymerized liposomal nanoparticle further comprises a targeting agent, for example on the surface of the HPLN. In some embodiments, the HPLNs include both, a therapeutic agent and a targeting agent.

Various embodiments of the present invention provide a method of treating, preventing the relapse of, reducing the severity of and/or slowing the progression of Burkitt lymphoma in a subject. The method comprises or consists of providing a hybrid polymerized liposomal nanoparticle described herein and administering a therapeutically effective amount of the hybrid polymerized liposomal nanoparticle to the subject, thereby treating, preventing the relapse of, reducing the severity of and/or slowing the progression of Burkitt lymphoma in the subject. In accordance with the present invention, the hybrid polymerized liposomal nanoparticles further include a therapeutic agent loaded inside the HPLN. Still in accordance with the present invention, the hybrid polymerized liposomal nanoparticle further comprises a targeting agent, for example on the surface of the HPLN. In some embodiments, the HPLNs include both, a therapeutic agent and a targeting agent.

Various embodiments of the present invention provide a method of treating, preventing the relapse of, reducing the severity of and/or slowing the progression of chronic myelogenous leukemia (CML) in a subject. The method comprises or consists of providing a hybrid polymerized liposomal nanoparticle described herein and administering a therapeutically effective amount of the hybrid polymerized liposomal nanoparticle to the subject, thereby treating, preventing the relapse of, reducing the severity of and/or slowing the progression of CML in the subject. In accordance with the present invention, the hybrid polymerized liposomal nanoparticles further include a therapeutic agent loaded inside the HPLN. Still in accordance with the present invention, the hybrid polymerized liposomal nanoparticle further comprises a targeting agent, for example on the surface of the HPLN. In some embodiments, the HPLNs include both, a therapeutic agent and a targeting agent.

Various embodiments of the present invention provide a method of treating, preventing the relapse of, reducing the severity of and/or slowing the progression of acute myeloid leukemia (AML) in a subject. The method comprises or consists of providing a hybrid polymerized liposomal nanoparticle described herein and administering a therapeutically effective amount of the hybrid polymerized liposomal nanoparticle to the subject, thereby treating, preventing the relapse of, reducing the severity of and/or slowing the progression of AML in the subject. In accordance with the present invention, the hybrid polymerized liposomal nanoparticles further include a therapeutic agent loaded inside the HPLN. Still in accordance with the present invention, the hybrid polymerized liposomal nanoparticle further comprises a targeting agent, for example on the surface of the HPLN. In some embodiments, the HPLNs include both, a therapeutic agent and a targeting agent.

Various embodiments of the present invention provide a method of treating, preventing the relapse of, reducing the severity of and/or slowing the progression of myelodysplastic syndromes (MDS) in a subject. The method comprises or consists of providing a hybrid polymerized liposomal nanoparticle described herein and administering a therapeutically effective amount of the hybrid polymerized liposomal nanoparticle to the subject, thereby treating, preventing the relapse of, reducing the severity of and/or slowing the progression of MDS in the subject. In accordance with the present invention, the hybrid polymerized liposomal nanoparticles further include a therapeutic agent loaded inside the HPLN. Still in accordance with the present invention, the hybrid polymerized liposomal nanoparticle further comprises a targeting agent, for example on the surface of the HPLN. In some embodiments, the HPLNs include both, a therapeutic agent and a targeting agent.

Various embodiments of the present invention provide a method of treating, preventing the relapse of, reducing the severity of and/or slowing the progression of any one or more of osteosarcoma, neuroblastoma or glioma in a subject. The method comprises or consists of providing a hybrid polymerized liposomal nanoparticle described herein and administering a therapeutically effective amount of the hybrid polymerized liposomal nanoparticle to the subject, thereby treating, preventing the relapse of, reducing the severity of and/or slowing the progression of any one or more of osteosarcoma, neuroblastoma or glioma in the subject. In accordance with the present invention, the hybrid polymerized liposomal nanoparticles further include a therapeutic agent loaded inside the HPLN. Still in accordance with the present invention, the hybrid polymerized liposomal nanoparticle further comprises a targeting agent, for example on the surface of the HPLN. In some embodiments, the HPLNs include both, a therapeutic agent and a targeting agent.

Various embodiments of the present invention provide a pharmaceutical composition comprising a hybrid polymerized liposomal nanoparticle described herein. Various embodiments of the present invention provide a pharmaceutical composition comprising two or more hybrid polymerized liposomal nanoparticles described herein. Various embodiments of the present invention provide a pharmaceutical composition comprising a plurality of hybrid polymerized liposomal nanoparticles described herein. In accordance with the present invention, the hybrid polymerized liposomal nanoparticle further comprises a therapeutic agent loaded therein or a targeting agent conjugated thereto. In accordance with the present invention, the hybrid polymerized liposomal nanoparticle further comprises a therapeutic agent loaded therein and a targeting agent conjugated thereto.

Various embodiments of the present invention provide a kit for treating, preventing, reducing the severity of and/or slowing the progression of a condition in a subject. The kit comprises a quantify of a hybrid polymerized liposomal nanoparticle described herein and instructions for using the hybrid polymerized liposomal nanoparticle to treat, prevent, reduce the severity of and/or slow the progression of the condition in the subject. In one embodiment, the hybrid polymerized liposomal nanoparticle further comprises a therapeutic agent loaded therein. In another embodiment, the hybrid polymerized liposomal nanoparticle further comprises a targeting agent conjugated thereto. In still another embodiment, the hybrid polymerized liposomal nanoparticle further comprises a therapeutic agent loaded therein and a targeting agent conjugated thereto.

Various compositions, methods and kits of the present invention find utility in the treatment of various conditions, including but not limited to various cancers.

BRIEF DESCRIPTION OF THE DRAWINGS

Exemplary embodiments are illustrated in referenced figures. It is intended that the embodiments and figures disclosed herein are to be considered illustrative rather than restrictive.

(FIG. 1A) a schematic representation of the hypothesized polymer "islands" in the HPLN membrane; (FIG. 1B) depiction of the process of passive vs. active loading of Doxorubicin into the HPLN (FIG. 1C) the average particle size of the drug loaded, antibody targeted HPLN by dynamic light scattering; (FIG. 1D) the particle stability with respect to drug leakage rate of over a 20 day time period.

FIG. 2 depicts, in accordance with various embodiments of the invention, specific binding and cellular uptake of targeted anti-CD99 conjugated HPLN. Top panel depicts FACS analysis showing specific binding to TC32 cells (Ewing tumor cells) and bottom panel shows fluorescence microscope image indicating cellular uptake.

FIG. 5 depicts, in accordance with various embodiments of the invention, that the tumor size and burden are markedly reduced. Starting at day 10 after REH-Luc leukemia tumor cell implantation mice in control group received only buffer treatment by IV administration, mice in once or twice per week groups received (targeted) anti-CD-19/HPLN/DOX (2 mg Dox/kg). Top panel: Xenogen camera images of treated and control mice at day 28. Color bar from red (biggest tumor mass) to purple (smallest tumor mass) gives a relative tumor size comparison. Bottom panel: Log scale of the relative tumor burden over the time course from day 0 to day 28, as estimated from the Xenogen images.

FIG. 9A-FIG. 9B depicts, in accordance with various embodiments of the invention, the efficacy response of anti-CD19-HPLN/Dox administered to a xenograft mouse model of leukemia made by tail vein injection of 1 million or 6 million REH-Luc cells. Treatments started on either the 3rd day or 10th day after injection of leukemia cells. (FIG. 9A) Day 19 results and (FIG. 9B) Day 28 results. Metastatic tumor burden was estimated from Xenogen camera images. The mice were treated with anti-CD19-HPLN by IV administration containing 2 mg/kg Doxorubicin either once or twice per week. Tumor images were made from both of dorsal and ventral side after the injection of luciferin once a week. The total tumor burden was calculated from the summation of both sides.

DETAILED DESCRIPTION OF THE INVENTION

Figure 1A:
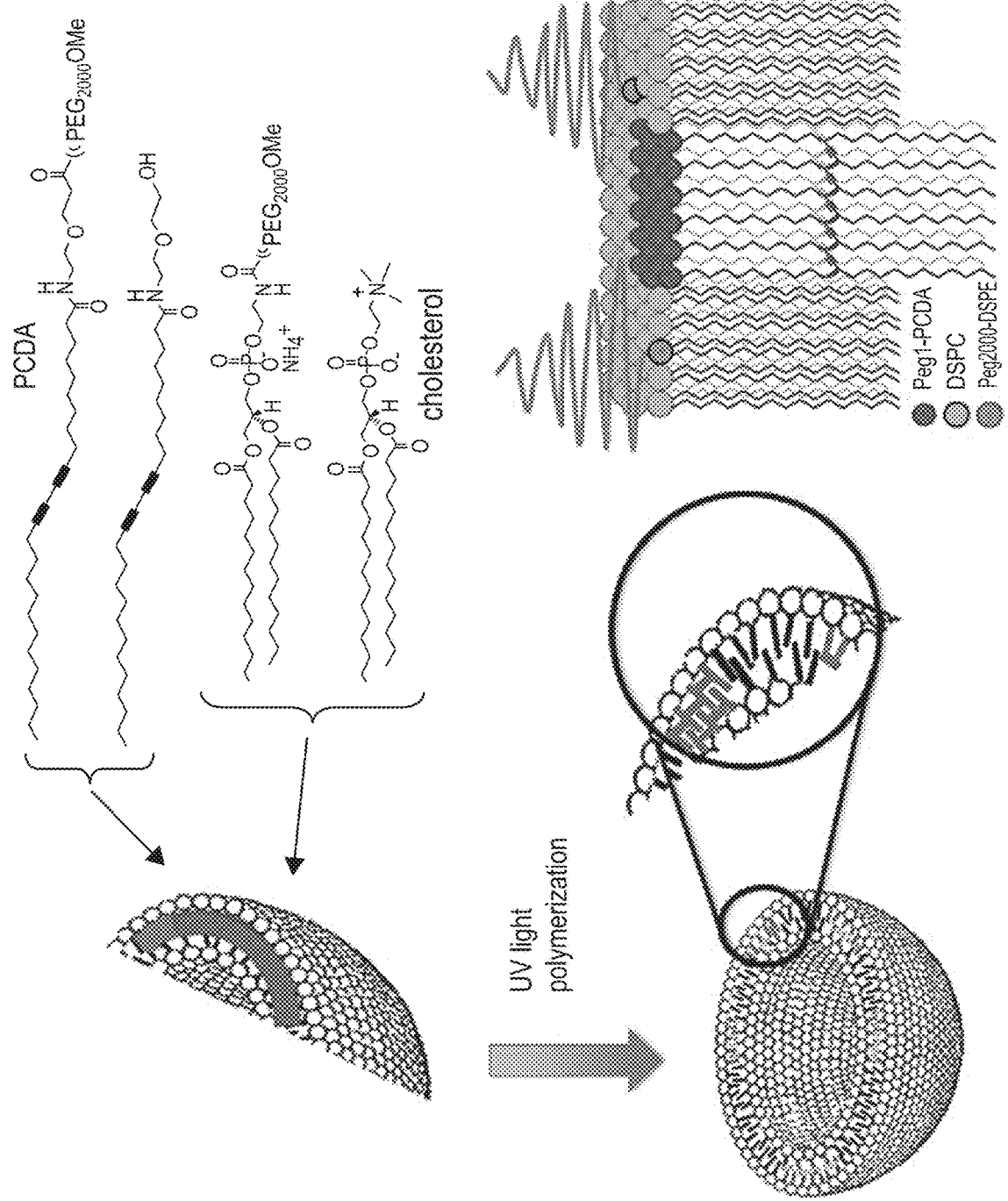
FIG. 1A-FIG. 1D depicts, in accordance with various embodiments of the invention, an embodiment of the HPLN drug delivery system.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* $22^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* $3^{rd}$ ed., revised ed., J. Wiley & Sons (New York, N.Y. 2006); Smith, *March's Advanced Organic Chemistry Reactions, Mechanisms and Structure* $7^{th}$ ed., J. Wiley & Sons (New York, N.Y. 2013); Singleton, *Dictionary of DNA and Genome Technology* 3rd ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* $2^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December), and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of leukemia, delay or slowing of leukemia, and amelioration or palliation of symptoms associated with leukemia.

"Conditions" and "disease conditions," as used herein may include, but are in no way limited to any form of malignant neoplastic cell proliferative disorders or diseases. Examples of such disorders include but are not limited to cancer and tumor.

A "cancer" or "tumor" as used herein refers to an uncontrolled growth of cells which interferes with the normal functioning of the bodily organs and systems, and/or all neoplastic cell growth and proliferation, whether malignant or benign, and all pre-cancerous and cancerous cells and tissues. A subject that has a cancer or a tumor is a subject having objectively measurable cancer cells present in the subject's body. Included in this definition are benign and malignant cancers, as well as dormant tumors or micrometastasis. Cancers which migrate from their original location and seed vital organs can eventually lead to the death of the subject through the functional deterioration of the affected organs. As used herein, the term "invasive" refers to the ability to infiltrate and destroy surrounding tissue. Melanoma is an invasive form of skin tumor. As used herein, the term "carcinoma" refers to a cancer arising from epithelial cells. A sarcoma is a cancer that arises from transformed cells of mesenchymal origin. Thus, malignant tumors made of cancerous bone, cartilage, fat, muscle, vascular, or hematopoietic tissues are, by definition, considered sarcomas. This is in contrast to a malignant tumor originating from epithelial cells, which are termed carcinoma. Sarcomas are given a number of different names based on the type of tissue that they most closely resemble. For example, osteosarcoma resembles bone, chondrosarcoma resembles cartilage, liposarcoma resembles fat, and leiomyosarcoma resembles smooth muscle. Examples of cancer include, but are not limited to, leukemia, sarcoma, Ewing sarcoma, osteosarcoma, nervous system tumor, brain tumor, nerve sheath tumor, breast cancer, colon cancer, carcinoma, lung cancer, hepatocellular cancer, gastric cancer, pancreatic cancer, cervical cancer, ovarian cancer, liver cancer, bladder cancer, cancer of the urinary tract, thyroid cancer, renal cancer, renal cell carcinoma, carcinoma, melanoma, head and neck cancer, brain cancer, and prostate cancer, including but not limited to androgen-dependent prostate cancer and androgen-independent prostate cancer. Examples of brain tumor include, but are not limited to, benign brain tumor, malignant brain tumor, primary brain tumor, secondary brain tumor, metastatic brain tumor, glioma, glioblastoma multiforme (GBM), medulloblastoma, ependymoma, astrocytoma, pilocytic astrocytoma, oligodendroglioma, brainstem glioma, optic nerve glioma, mixed glioma such as oligoastrocytoma, low-grade glioma, high-grade glioma, supratentorial glioma, infratentorial glioma, pontine glioma, meningioma, pituitary adenoma, and nerve sheath tumor. Nervous system tumor or nervous system neoplasm refers to any tumor affecting the nervous system. A nervous system tumor can be a tumor in the central nervous system (CNS), in the peripheral nervous system (PNS), or in both CNS and PNS. Examples of nervous system tumor include but are not limited to brain tumor, nerve sheath tumor, and optic nerve glioma. Leukemia is a type of cancer of the blood or bone marrow characterized by an abnormal increase of immature white blood cells called "blasts". Examples of leukemia include but are not limited to acute leukemia, chronic leukemia, lymphocytic leukemia, myelogenous leukemia, acute lymphocytic leukemia (ALL), chronic lymphocytic leukemia (CLL), acute myelogenous leukemia (AML), chronic myelogenous leukemia (CML), hairy cell leukemia (HCL), T-cell prolymphocytic leukemia (T-PLL), acute promyleocytic leukemia, large granular lymphocytic leukemia, and adult T-cell leukemia.

As used herein, the term "administering," refers to the placement an agent as disclosed herein into a subject by a method or route that results in at least partial localization of the agents at a desired site. "Route of administration" may refer to any administration pathway known in the art, including but not limited to aerosol, nasal, oral, transmucosal, transdermal, parenteral, enteral, topical or local. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release.

The term "sample" or "biological sample" as used herein denotes a sample taken or isolated from a biological organism, e.g., a tumor sample from a subject. Exemplary biological samples include, but are not limited to, a biofluid sample; serum; plasma; urine; saliva; a tumor sample; a tumor biopsy and/or tissue sample etc. The term also includes a mixture of the above-mentioned samples. The term "sample" also includes untreated or pretreated (or pre-processed) biological samples. In some embodiments, a sample can comprise one or more cells from the subject. In some embodiments, a sample can be a tumor cell sample, e.g. the sample can comprise cancerous cells, cells from a tumor, and/or a tumor biopsy.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

A subject can be one who has been previously diagnosed with or identified as suffering from or having a condition in need of treatment (e.g., leukemia) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. A "subject in need" of treatment for a particular condition can be a subject suspected of having that condition, diagnosed as having that condition, already treated or being treated for that condition, not treated for that condition, or at risk of developing that condition.

The term "statistically significant" or "significantly" refers to statistical evidence that there is a difference. It is defined as the probability of making a decision to reject the null hypothesis when the null hypothesis is actually true. The decision is often made using the p-value.

As used herein, "variants" can include, but are not limited to, those that include conservative amino acid mutations, SNP variants, splicing variants, degenerate variants, and biologically active portions of a gene. A "degenerate variant" as used herein refers to a variant that has a mutated nucleotide sequence, but still encodes the same polypeptide due to the redundancy of the genetic code. In accordance with the present invention, an antibody protein (e.g., an anti-CD19 antibody) may be modified, for example, to facilitate or improve identification, expression, isolation, storage and/or administration, so long as such modifications do not reduce the antibody protein's function to unacceptable level. In various embodiments, a variant of the antibody protein has at least 10%, 20%, 30%, 40%, 50%, 60%, 70%, 80%, 90%, or 95% of the function of a wild-type antibody protein.

The term "functional" when used in conjunction with "equivalent", "analog", "derivative", "variant" or "fragment" refers to an entity or molecule which possess a biological, physical, and/or chemical activity that is substantially similar to a biological, physical, and/or chemical activity of the entity or molecule of which it is an equivalent, analog, derivative, variant or fragment thereof.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Targeted nanodelivery systems may be invaluable in increasing the therapeutic window and minimizing systemic therapy related toxicity. This is particularly important in treating metastatic diseases that ultimately kill most cancer patients. Unlike solid tumors, for which surgery, radiation, and conventional treatments are an option, leukemias are cancers of the blood, which have very poor prognosis due to the fact that they are disseminated diseases from inception. For these diseases, it is not possible to achieve tumoricidal doses without also killing too much of the normal tissue. Thus, even more so than in the treatment of solid tumors, an innovative technology solution is required to increase the partition of drug delivery between tumor and normal tissue. The current success in cancer therapy using drugs which can inhibit the specific pathways improves the survival rate of patients but unfortunately it is not the case of all cancers and still many different kinds of cancers continue to have a poor prognosis. Furthermore the incompleteness of cancer therapies causes a variety of side effects such as secondary cancers, heart or lung damage, infertility or chronic hepatitis. Therefore a reliable tumor specific therapy is urgently needed to treat cancer patients. It is widely recognized that the recent chemotherapy could be far more effective if higher doses could be specifically delivered to the tumor and not to normal tissues.

Accordingly, provided herein are hybrid polymerized liposomal nanoparticles comprising or consisting of a polymerizable lipid and a non-polymerizable lipid. In various embodiments, the polymerizable lipid comprises or consists of at least one PEGylated polymerizable lipid having a PEG polymer chain. The advantage of the HPLNs described herein is that the presence of PEGylated polymerizable lipid having a PEG polymer chain significantly increases the stability of the HPLNs. For example, the initial PLN formulations were composed entirely of 10,12-pentacosadiynoic acid (PCDA) derivatives (or diacetylene containing lipids) and when polymerized and subsequently heated above 50 degrees C. formed a very fluorescent particle that could easily be detected. However, these nanoparticles proved problematic when trying to adapt them for delivery of therapeutic agents. Attempts at effectively loading them with cytotoxic chemotherapeutic agents, through encapsulation across ion gradients using the pre-polymerized liposomes, failed to allow even modest levels of drug to be loaded. The hybrid PLNs described herein, which include polymerizable lipid having at least one PEGylated polymerizable lipid having a PEG polymer chain, overcome the aforementioned problems and can be effectively used to deliver therapeutic agents to target cells.

Without wishing to be bound by any particular theory, the inventors posit that the lipid components may phase separate on the surface of the PLNs (for example, the surface of the PLNs looks as if islands of polymer patches are surrounded by seas of non-polymerizable lipid membrane). These islands, once formed, could act as points of stickiness between particles and contribute to the aggregation of the nanoparticles, leading to formulation instability. To solve this problem, as described herein, the inventors introduced PEG2000-10, 12-pentacosadiynoic acid derivatives (polymerizable lipids containing a PEG 2000 group) in to the polymerizable lipid component, resulting in incorporation of PEG groups on their surfaces, thus addressing the size instability problems. In contrast, the earlier PLN formulation (for example, as described in WO 2012155021), the "polymer island" forming lipids have no or minimal PEG groups attached to them, and this may contribute to the size instability of the particles (e.g. aggregation).

Increasing the amount of polymerizable lipid or polymer amount in the HPLN formulation seems to improve the efficacy of the particle in terms of tumor kill. By the same token, increasing the amount of polymerizable lipid or polymer amount decreases the amount of drug we can load into the particles. Thus, both curves (good efficacy AND high drug load) will maximize at certain values, as determined by cell-based and animal experiments. Herein, we demonstrate that the L-α-distearoyl phosphotidylcholine lipid must be between 10 mole % and 60 mole %.

In must be recognized that the micelle lipid insertion method is one possible means for appending targeting molecules on the HPLN surface. Another method is to formulate the HPLN lipid mixture initially with the inclusion of maleimide-terminated PEG2000 lipids (e.g. Mal-PEG2000-L-α-distearoyl phosphotidylethanolamine: mal-PEG2000-DSPE or Mal-PEG2000-PCDA). Once the HPLN is formed, the targeting molecule can be directly attached to the surface maleimide groups. Since the micelle insertion method is self-limiting, meaning that at a certain PEG level on the HPLN surface (about 5 mol %), no more PEGylated lipids can insert themselves. If one wanted a PEG2000 surface level that exceeded about 5%, the micelle insertion method would not be applicable. Only the method where one formulates the liposome initially with the PEG2000 lipid component >5 mol % could be used to construct these HPLNs.

Hybrid Polymerized Liposomal Nanoparticles (HPLNs)

In various embodiments, the present invention provides a hybrid polymerized liposomal nanoparticle (HPLN). The HPLN may comprise or consist of a polymerizable lipid and a non-polymerizable lipid. The polymerizable lipid comprises at least one PEGylated polymerizable lipid having a PEG polymer chain. In an embodiment, the HPLN further comprises one or more therapeutic agent, as described herein, encapsulated in the HPLN. In an embodiment, the HPLN further comprises one or more antibodies conjugated to the HPLN. In an embodiment, the HPLN comprises one or more therapeutic agents encapsulated in the HPLN and one or more antibodies conjugated to the HPLN.

In various embodiments, the present invention provides a hybrid polymerized liposomal nanoparticle (HPLN). The PLN may comprise or consist of a polymerizable lipid (about 15-40 mol %) and non-polymerizable lipids. The polymerizable lipid comprises at least one PEGylated polymerizable lipid having a PEG polymer chain. The non-polymerizable lipid comprises a zwitterionically charged lipid (at least about 10 mol %), a neutrally charged molecule (about 20-45 mol %) and a negatively charged lipid (about 1-15 mol %). In an embodiment, the HPLN further comprises one or more therapeutic agent(s), as described herein, encapsulated in the HPLN. In an embodiment, the HPLN further comprises one or more antibodies conjugated to the HPLN. In an embodiment, the HPLN comprises one or more therapeutic agents encapsulated in the HPLN and one or more antibodies conjugated to the HPLN.

In various embodiments, the present invention provides a hybrid polymerized liposomal nanoparticle (HPLN). The HPLN may comprise or consist of a polymerizable lipid (about 15 mol %) and non-polymerizable lipids. The polymerizable lipid comprises at least one PEGylated polymerizable lipid having a PEG polymer chain. The non-polymerizable lipids comprise a zwitterionically charged lipid (about 47 mol %), a neutrally charged molecule (about 32 mol %) and a negatively charged lipid (about 6 mol %). In an embodiment, the HPLN further comprises one or more therapeutic agent, as described herein, encapsulated in the HPLN. In an embodiment, the HPLN further comprises one or more antibodies conjugated to the HPLN. In an embodiment, the HPLN comprises one or more therapeutic agents encapsulated in the HPLN and one or more antibodies conjugated to the HPLN.

In various embodiments, the present invention provides a hybrid polymerized liposomal nanoparticle (HPLN). The HPLN may comprise or consist of a polymerizable lipid (about 15 mol %) and non-polymerizable lipids. The polymerizable lipid comprises at least one PEGylated polymerizable lipid having a PEG polymer chain (about 1 mol %). The non-polymerizable lipids comprise a zwitterionically charged lipid (about 51 mol %); a neutrally charged molecule (about 32 mol %); and a negatively charged lipid (about 2 mol %). In an embodiment, the HPLN further comprises one or more therapeutic agent, as described herein, encapsulated in the HPLN. In an embodiment, the HPLN further comprises one or more antibodies conjugated to the HPLN. In an embodiment, the HPLN comprises one or more therapeutic agents encapsulated in the HPLN and one or more antibodies conjugated to the HPLN.

In various embodiments, the present invention provides a hybrid polymerized liposomal nanoparticle, comprising about 14 mol % h-PEG1PCDA, about 51 mol % hydrogenated soy PC, about 32 mol % cholesterol, about 2 mol % m-PEG2000-DSPE, and about 1 mol % m-PEG2000-PCDA. In an embodiment, the HPLN further comprises one or more therapeutic agent, as described herein, encapsulated in the HPLN. In an embodiment, the HPLN further comprises one or more antibodies conjugated to the HPLN. In an embodiment, the HPLN comprises one or more therapeutic agents encapsulated in the HPLN and one or more antibodies conjugated to the HPLN. In some embodiments, hybrid polymerized liposomal nanoparticle may be used to treat any one or more of Ewing sarcoma, Burkitt lymphoma, osteosarcoma, neuroblastoma, glioma, ALL, CML, AML or MDS.

In various embodiments, the present invention provides a hybrid polymerized liposomal nanoparticle, comprising about 14 mol % h-PEG1PCDA, about 48 mol % hydrogenated soy PC, about 32 mol % cholesterol, about 2 mol % m-PEG2000-DSPE, about 3 mol % mal-PEG2000-DSPE, and about 1 mol % m-PEG2000-PCDA. In an embodiment, the HPLN further comprises one or more therapeutic agent, as described herein, encapsulated in the HPLN. In an embodiment, the HPLN further comprises one or more antibodies conjugated to the HPLN. In an embodiment, the HPLN comprises one or more therapeutic agents encapsulated in the HPLN and one or more antibodies conjugated to the HPLN. In some embodiments, hybrid polymerized liposomal nanoparticle may be used to treat any one or more of Ewing sarcoma, Burkitt lymphoma, osteosarcoma, neuroblastoma, glioma, ALL, CML, AML or MDS.

In various embodiments, the present invention provides a hybrid polymerized liposomal nanoparticle, comprising about 24 mol % h-PEG1PCDA, about 41 mol % hydrogenated soy PC, about 32 mol % cholesterol, about 2 mol % m-PEG2000-DSPE, and about 1 mol % m-PEG2000-PCDA. In an embodiment, the HPLN further comprises one or more therapeutic agent, as described herein, encapsulated in the HPLN. In an embodiment, the HPLN further comprises one or more antibodies conjugated to the HPLN. In an embodiment, the HPLN comprises one or more therapeutic agents encapsulated in the HPLN and one or more antibodies conjugated to the HPLN. In some embodiments, hybrid polymerized liposomal nanoparticle may be used to treat any one or more of Ewing sarcoma, Burkitt lymphoma, osteosarcoma, neuroblastoma, glioma, ALL, CML, AML, or MDS.

In various embodiments, the neutrally charged molecule is cholesterol, ergosterol, hopanoids, phytosterol, stanol, and sterols, and functional derivatives thereof.

In various embodiments, the hybrid polymerized liposomal nanoparticle provided herein is about 30-200 nm in size. In various embodiments, the hybrid polymerized liposomal nanoparticle provided herein is UV treated for about 1-35 minutes after fabrication to polymerize the polymerizable lipid. In various embodiments, the hybrid polymerized liposomal nanoparticle provided herein is prepared by overnight cooling at 5-10° C. immediately after extrusion but prior to polymerization.

In various embodiments, the hybrid polymerized liposomal nanoparticle provided herein has a circulation half-life of at least about 3 to at least about 4 hours. In various embodiments, the hybrid polymerized liposomal nanoparticle provided herein is internalized into the endosome compartment of a cell after about 30 minutes In various embodiments, the PEGylated polymerizable lipid having a PEG polymer chain is about 0.1-1, 1-5, 5-10, or 10-15 mol % of the PLN. In various embodiments, the PEG polymer chain comprises about 10-150, 10-50, 50-100, or 100-150 PEG units. In various embodiments, the molecular weight of the PEG polymer chain is about 500-5000, 500-2000, or 2000-5000 Da. In various embodiments, the PEGylated polymerizable lipid is selected from the group consisting (PEG)n-10,12-pentacosadiynoic acid ((PEG)n-PCDA) derivatives, wherein n is the number of the PEG units in the PEG polymer chain and is about 10-150, 10-50, 50-100, or 100-150. In various embodiments, the PEGylated polymerizable lipid is selected from the group consisting PEG(mw)-10,12-pentacosadiynoic acid (PEG(mw)-PCDA) derivatives, wherein mw is the molecular weight of the PEG polymer chain and is about 500-5000, 500-2000, or 2000-5000 Da. In certain embodiments, the PEGylated polymerizable lipid is PEG2000-10-12-pentacosadiynamide or PEG2000-10-12-pentacosadiynoic acid. Examples of PEGylated polymerizable lipids include but are not limited to, PEGylated Diyne PC, PEGylated Diyne PE, and PEGylated 10,12-pentacosadiynoic acid (PEG-PCDA) and their functional derivatives and analogs. In some embodiments, the PEGylated polymerizable lipid may comprise a PEGylated polymerizable group attached to a lipid molecule.

In various embodiments, the hybrid polymerized liposomal nanoparticle provided herein comprises at least 0.1, 0.5, 1, 5, or 10 mol % of PEGylated polymerizable lipids. In some embodiments, the hybrid polymerized liposomal nanoparticle provided herein comprises at least 1 mol % of PEGylated polymerizable lipids. In other embodiments, the hybrid polymerized liposomal nanoparticle provided herein comprises at least 10 mol % of PEGylated polymerizable lipids.

In various embodiments, the hybrid polymerized liposomal nanoparticle provided herein may comprise a lipid conjugated to a functional moiety. Examples of functional moieties include but are not limited to targeting agents, imaging agents, and therapeutic agents, and their combinations. In various embodiments, the hybrid polymerized liposomal nanoparticle provided herein may comprise a lipid with a positive, negative, or neutral charge.

In various embodiments, the polymerizable lipid is about 15-40 mol % of the PLN. In various embodiments, the polymerizable lipid comprises an unsaturated lipid. In various embodiments, the polymerizable lipid comprises a diacetylenic lipid. In various embodiments, the polymerizable lipid comprises N-(5'-hydroxy-3'-oxypentyl)-10-12-pentacosadiynamide (h-PEG1-PCDA), N-(5'-sulfo-3'-oxypentyl)-10-12-pentacosadiynamide (sulfo-PEG1-PCDA), N-[methoxy(polyethylene glycol)-750]-10-12-pentacosadiynamide (m-PEG750-PCDA), or N-[maleimide(polyethylene glycol)-1500]-10-12-pentacosadiynamide (mal-PEG1500-PCDA), or a combination thereof. In various embodiments, the polymerizable lipid is a C25 tail lipid.

In various embodiments, the non-polymerizable lipid is about 80-85 mol % of the HPLN. In various embodiments, the non-polymerizable lipid is about 75-85 mol % of the HPLN. In various embodiments, the non-polymerizable lipid is about 30-60 mol % of the HPLN. In various embodiments, the non-polymerizable lipid comprises a saturated phospholipid. In various embodiments, the non-polymerizable lipid comprises at least one PEGylated non-polymerizable lipid having a PEG polymer chain. In various embodiments, the non-polymerizable lipid comprises L-α-phosphatidylcholine hydrogenated soy (hydrogenated soy PC), distearoylphosphatidylcholine (DSPC), cholesterol, 1,2-distearoyl-sn-glycero-3-phosphoethanolamine-N-[methoxy(polyethylene glycol)-2000] (m-Peg2000-DSPE), or 1,2-distearoyl-sn-glycero-3-phosphoethanolamine-N-[maleimide(polyethylene glycol)-2000] (mal-Peg2000-DSPE), or a combination thereof. In various embodiments, the non-polymerizable lipid comprises L-α-phosphatidylcholine, PE-PEG2000-1,2-distearoyl-sn-glycero-3-phosphoethanolamine-N-[methoxy(polyethylene glycol)-2000], or PE-PEG2000-biotin, or a combination thereof. In various embodiments, the non-polymerizable lipid is a C18 tail lipid.

In various embodiments, the hybrid polymerized liposomal nanoparticle provided herein comprises a zwitterionically charged lipid at at least about 10 mol %. In various embodiments, the hybrid polymerized liposomal nanoparticle provided herein comprises a zwitterionically charged lipid at about 10-20, 20-30, 30-40, 40-50, 50-60, 60-70, 70-80, or 80-90 mol %. In various embodiments, the hybrid polymerized liposomal nanoparticle provided herein comprises a zwitterionically charged lipid at about 10-30, 10-15, 15-20, 20-25, or 25-30 mol %. In accordance with various embodiments of the present invention, the zwitterionically charged lipid can comprise L-α-distearoylphosphatidylcholine, L-α-phosphatidylcholine hydrogenated soy (hydrogenated soy PC), or distearoylphosphatidylcholine (DSPC). Still in accordance with various embodiments of the present invention, the zwitterionically charged lipid is a C18 tail lipid.

In various embodiments, the hybrid polymerized liposomal nanoparticle provided herein further comprises a therapeutic agent loaded into the hybrid polymerized liposomal nanoparticle. In accordance with the present invention, non-limiting examples of the therapeutic agent include antineoplastic agents, blood products, biological response modifiers, anti-fungals, hormones, vitamins, peptides, antituberculars, enzymes, anti-allergic agents, anti-coagulators, circulatory drugs, metabolic potentiators, antivirals, antianginals, antibiotics, antiinflammatories, antiprotozoans, antirheumatics, narcotics, opiates, cardiac glycosides, neuromuscular blockers, sedatives, local anesthetics, general anesthetics, radioactive compounds, radiosensitizers, immune checkpoint inhibitors, monoclonal antibodies, genetic material, antisense nucleic acids such as siRNA or RNAi molecules, and prodrugs.

In various embodiments, the hybrid polymerized liposomal nanoparticle provided herein further comprises a chemotherapeutic agent loaded into the hybrid polymerized liposomal nanoparticle. In various embodiments, the hybrid polymerized liposomal nanoparticle provided herein further comprises two or more chemotherapeutic agents loaded into the hybrid polymerized liposomal nanoparticle. In various embodiments, the chemotherapeutic agent can be doxorubicin, irinotecan, cis-platin, topotecan, vincristine, mytomicin, paxlitaxol, cytarabine, mitoxantrone, Ara-C (cytarabine), VP-16 (etoposide), or siRNA, or a combination thereof.

In various embodiments, the hybrid polymerized liposomal nanoparticle provided herein further comprises a targeting agent conjugated to the surface of the hybrid polymerized liposomal nanoparticle. In various embodiments, the hybrid polymerized liposomal nanoparticle provided herein further comprises two or more targeting agents conjugated to the surface of the hybrid polymerized liposomal nanoparticle. In various embodiments, the targeting agent can be diabodies, antibodies, ligands, proteins, peptides, carbohydrates, vitamins, nucleic acids and combinations thereof. In various embodiments, the targeting agent is an anti-CD19 antibody, anti-CD34 antibody, anti-CD99 antibody, anti-CD117 antibody, anti-CD166 antibody, or anti-CA19-9 antibody, or a combination thereof. In various embodiments, the targeting agent is a peptide capable of specifically binding to a cell surface molecule. In accordance with the present invention, the cell surface molecule can be a cell membrane protein selected from the group consisting of structural proteins, cell adhesion molecules, membrane receptors, carrier proteins and channel proteins. Examples of the cell surface molecule include but are not limited to Activated Leukocyte Adhesion Molecule (CD-166), carbohydrate antigen 19-9 (CA19-9), Alphafetoprotein (AFP), Carcinoembryonic antigen (CEA), Ovarian cancer antigen (CA-125), breast cancer antigens (MUC-1 and epithelial tumor antigen (ETA)), Tyrosinase malignant melanoma antigen and Melanoma-associated antigen (MAGE), abnormal antigenic products of ras, p53, Ewing sarcoma antigen (CD-99), leukemia antigens (CD-19 and CD-117), Vascular Endothelial Growth Factor (VEGF), Epithelial Growth Factor Receptor (EGFR), Her2/neu, or prostate-specific membrane antigen (PSMA). In accordance with the present invention, the targeting agent (e.g., an antibody or a peptide) can be synthetic or from any source, e.g., rat, mouse, guinea pig, dog, cat, rabbit, pig, cow, horse, goat, donkey or human. In various embodiments, the targeting agent enhances endocytosis or cell membrane fusion.

In various embodiments, the hybrid polymerized liposomal nanoparticle provided herein further comprises an agent conjugated to the surface of the hybrid polymerized liposomal nanoparticle that will elicit an immune response as a treatment for cancer. In accordance with the present invention, the cell surface molecule can be a cell membrane protein selected from the group consisting of E6 and E7 proteins that are detectable in all Human Papilloma Virus (HPV)-positive pre-cancerous and cancer cells. Alternatively, mucin glycoproteins are important diagnostic and therapeutic targets for cancer treatment. Vaccines based on tumor associated MUC1 and MUC4 glycoproteins, an important tumor marker overexpressed in lung cancer and uniquely expressed in pancreatic ductal adenocarcinoma, are the result of aberrant glycosylation in tumor cells that results from an exposure of its peptide backbone and the formation of tumor-associated glycopeptide antigens. In various embodiments, the hybrid polymerized liposomal nanoparticle provided herein further comprises two or more antigens conjugated to the surface of the hybrid polymerized liposomal nanoparticle.

In various embodiments, the present invention provides a method loading a therapeutic agent into a hybrid polymerized liposomal nanoparticle described herein. The method comprises: providing a hybrid polymerized liposomal nanoparticle described herein; establishing an ion gradient across the membrane of the hybrid polymerized liposomal nanoparticle; providing a therapeutic agent; and incubating the therapeutic agent with the hybrid polymerized liposomal nanoparticle, thereby loading the therapeutic agent into the hybrid polymerized liposomal nanoparticle. In various embodiments, the ion gradient is an ammonium sulfate gradient and/or pH gradient. In accordance with the present invention, non-limiting examples of the therapeutic agent include antineoplastic agents, blood products, biological response modifiers, anti-fungals, hormones, vitamins, peptides, anti-tuberculars, enzymes, anti-allergic agents, anticoagulators, circulatory drugs, metabolic potentiators, antivirals, antianginal s, antibiotics, antiinflammatories, antiprotozoans, antirheumatics, narcotics, opiates, cardiac glycosides, neuromuscular blockers, sedatives, local anesthetics, general anesthetics, radioactive compounds, radiosensitizers, immune checkpoint inhibitors, monoclonal antibodies, genetic material, antisense nucleic acids such as siRNA or RNAi molecules, and prodrugs. In various embodiments, the therapeutic agent is a chemotherapeutic agent. In various embodiments, the chemotherapeutic agent can be doxorubicin, irinotecan, cis-platin, topotecan, vincristine, mytomicin, paxlitaxol, cytarabine, mitoxantrone, Ara-C (cytarabine), VP-16 (etoposide), or siRNA, or a combination thereof.

More examples of chemotherapeutic agents include but are not limited to Actinomycin, Alitretinoin, All-trans retinoic acid, Azacitidine, Azathioprine, Bevacizumab, Bexatotene, Bleomycin, Bortezomib, Carboplatin, Capecitabine, Cetuximab, Cisplatin, Chlorambucil, Cyclophosphamide, Cytarabine, Daunorubicin, Docetaxel, Doxifluridine, Doxorubicin, Epirubicin, Epothilone, Erlotinib, Etoposide, Fluorouracil, Gefitinib, Gemcitabine, Hydroxyurea, Idarubicin, Imatinib, Ipilimumab, Irinotecan, Mechlorethamine, Melphalan, Mercaptopurine, Methotrexate, Mitoxantrone, Ocrelizumab, Ofatumumab, Oxaliplatin, Paclitaxel, Panitumab, Pemetrexed, Rituximab, Tafluposide, Teniposide, Tioguanine, Topotecan, Tretinoin, Valrubicin, Vemurafenib, Vinblastine, Vincristine, Vindesine, Vinorelbine, Vorinostat, Romidepsin, 5-fluorouracil (5-FU), 6-mercaptopurine (6-MP), Cladribine, Clofarabine, Floxuridine, Fludarabine, Pentostatin, Mitomycin, ixabepilone, Estramustine, prednisone, methylprednisolone, dexamethasone or a combination thereof.

In various embodiments, the present invention provides a method of conjugating a targeting agent to a hybrid polymerized liposomal nanoparticle described herein. The method comprises: providing a lipid micelle; providing a targeting agent; conjugating the targeting agent to the lipid micelle; providing a hybrid polymerized liposomal nanoparticle described herein; and incubating the hybrid polymerized liposomal nanoparticle with the lipid micelle conjugated with the target agent, thereby transferring the targeting agent to the hybrid polymerized liposomal nanoparticle. In certain embodiments, the targeting agent is conjugated to the lipid micelle through a reaction between a thiol group on the targeting agent and a maleimide group on the lipid micelle. In various embodiments, the targeting agent can be diabodies, antibodies, ligands, proteins, peptides, carbohydrates, vitamins, nucleic acids and combinations thereof. In various embodiments, the targeting agent is an anti-CD19 antibody, anti-CD34 antibody, anti-CD99 antibody, anti-CD117 antibody, anti-CD166 antibody, or anti-CA19-9 antibody, or a combination thereof. In various embodiments, the targeting agent is a peptide capable of specifically binding to a cell surface molecule. In accordance with the present invention, the cell surface molecule can be a cell membrane protein selected from the group consisting of structural proteins, cell adhesion molecules, membrane receptors, carrier proteins and channel proteins. Examples of the cell surface molecule include but are not limited to Activated Leukocyte Adhesion Molecule (CD-166), carbohydrate antigen 19-9 (CA19-9), Alphafetoprotein (AFP), Carcinoembryonic antigen (CEA), Ovarian cancer antigen (CA-125), breast cancer antigens (MUC-1 and epithelial tumor antigen (ETA)), Tyrosinase malignant melanoma antigen and Melanoma-associated antigen (MAGE), abnormal antigenic products of ras, p53, Ewing sarcoma antigen (CD-99), leukemia antigens (CD-19 and CD-117), Vascular Endothelial Growth Factor (VEGF), Epithelial Growth Factor Receptor (EGFR), Her2/neu, or prostate-specific membrane antigen (PSMA). In accordance with the present invention, the targeting agent (e.g., an antibody or a peptide) can be synthetic or from any source, e.g., rat, mouse, guinea pig, dog, cat, rabbit, pig, cow, horse, goat, donkey or human.

In an embodiment, provided herein is a HPLN/Dox particles prepared by conjugating monoclonal antibodies that target the HPLN described herein to the CD-19 cell surface marker on human leukemia cells (REH cells). Chemically reduced anti-CD-19 antibodies were conjugated to micelles composed of maleimide-terminated and methoxy-terminated PEG2000 phospholipids [Iden and Allen, 2001]. Upon exposure to HPLN/Dox the PEG2000 phospholipid micelles, with a portion labeled by anti-CD-19 antibodies, insert into the HPLN membrane to yield anti-CD-19/HPLN/Dox particles. The targeted particles were purified by size filtration to remove unconjugated antibodies and other small, molecular weight impurities. Prior to the inventors, no one has even demonstrated that Pegylated micelle lipids could intercalate into polymer-containing liposomes, especially the HPLN described herein having PEG2000 polymer islands for resisting stickiness between particles. Indeed, one might expect the presence of the polymer to inhibit the process. As the amount of polymer is increased, one might expect the insertion process to become inhibited. However, within the range of polymer component described in this application, our results demonstrate no such effect.

Targeted nanoparticles have shown the potential to deliver the anticancer drugs to cancer cells selectively and to overcome unexpected cytotoxicity and limited efficacy of the chemotherapy caused by the unselective delivery to the normal cells. Herein, a novel nanoparticle (HPLN) was used for the treatment of childhood and adult ALL and Ewing sarcoma. AntiCD19 and antiCD99 antibodies were used for targeting of ALL and Ewing tumor, respectively. These tumor-specific HPLNs effectively inhibit tumor growth in a murine model. Removal of targeting antibody or drug eliminates the antitumor effects, which proves this anticancer effect of HPLN is very specific to the target cancer cells and dependent upon drug. No abnormalities in liver and kidney function tests, complete blood counts or pathology of major organs are observed from tail-vein administrations. These targeted HPLNs showed much better cytotoxicity over a conventional untargeted PEG-liposomal Doxorubicin formulation (Doxil®). Additionally the targeted HPLN could be found in the tumor cells in a murine model. Thus, this indicates a safe and efficient targeted HPLN delivery system of anticancer drugs to, for example, childhood and adult ALL and Ewing Sarcoma subjects.

Treatment Methods

In various embodiments, the present invention provides a method of treating, preventing, reducing the likelihood of having, reducing the severity of and/or slowing the progression of a condition in a subject. The method may comprise or may consist of providing a hybrid polymerized liposomal nanoparticle described herein and administering a therapeutically effective amount of the hybrid polymerized liposomal nanoparticle to the subject, thereby treating, preventing, reducing the likelihood of having, reducing the severity of and/or slowing the progression of the condition in the subject. In various embodiments, the condition is Ewing sarcoma, Burkitt lymphoma, osteosarcoma, neuroblastoma, glioma, ALL, CML, AML or MDS. In some embodiments, the methods may further comprise simultaneously or sequentially providing additional therapies including by not limited to chemotherapy, radiation or a combination thereof.

In various embodiments, the condition is a cancer. Examples of cancer include but are not limited to breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; cervical cancers such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; acute myeloid leukemia (AML), preferably acute promyleocytic leukemia in peripheral blood; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's sarcoma; Ewing sarcoma; central nervous system cancers such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas; oral cavity and oropharyngeal cancer; stomach cancer such as lymphomas, gastric stromal tumors, and carcinoid tumors; testicular cancer such as germ cell tumors (GCTs), which include seminomas and nonseminomas; and gonadal stromal tumors, which include Leydig cell tumors and Sertoli cell tumors; and thymus cancer, such as to thymomas, thymic carcinomas, Hodgkin disease, non-Hodgkin lymphomas carcinoids or carcinoid tumors. Also, the methods can be used to treat viral-induced cancers. The major virus-malignancy systems include hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer.

In various embodiments, the subject is a human. In various embodiments, the subject is a mammalian subject including but not limited to human, monkey, ape, dog, cat, cow, horse, goat, pig, rabbit, mouse and rat. In some embodiments, the subject has consistent microbial infection including but not limited to bacterial, viral, fungal and parasitic infections.

In accordance with the present invention, the hybrid polymerized liposomal nanoparticle comprises a therapeutic agent loaded inside. In accordance with the present invention, non-limiting examples of the therapeutic agent include antineoplastic agents, blood products, biological response modifiers, anti-fungals, hormones, vitamins, peptides, antituberculars, enzymes, anti-allergic agents, anti-coagulators, circulatory drugs, metabolic potentiators, antivirals, antianginals, antibiotics, antiinflammatories, antiprotozoans, antirheumatics, narcotics, opiates, cardiac glycosides, neuromuscular blockers, sedatives, local anesthetics, general anesthetics, radioactive compounds, radiosensitizers, immune checkpoint inhibitors, monoclonal antibodies, genetic material, antisense nucleic acids such as siRNA or RNAi molecules, and prodrugs. In various embodiments, the therapeutic agent is a chemotherapeutic agent. In various embodiments, the chemotherapeutic agent can be doxorubicin, irinotecan, cis-platin, topotecan, vincristine, mytomicin, paxlitaxol, cytarabine, mitoxantrone, Ara-C (cytarabine), VP-16 (etoposide), or siRNA, or a combination thereof.

More examples of chemotherapeutic agents include but are not limited to Actinomycin, Alitretinoin, All-trans retinoic acid, Azacitidine, Azathioprine, Bevacizumab, Bexatotene, Bleomycin, Bortezomib, Carboplatin, Capecitabine, Cetuximab, Cisplatin, Chlorambucil, Cyclophosphamide, Cytarabine, Daunorubicin, Docetaxel, Doxifluridine, Doxorubicin, Epirubicin, Epothilone, Erlotinib, Etoposide, Fluorouracil, Gefitinib, Gemcitabine, Hydroxyurea, Idarubicin, Imatinib, Ipilimumab, Irinotecan, Mechlorethamine, Melphalan, Mercaptopurine, Methotrexate, Mitoxantrone, Ocrelizumab, Ofatumumab, Oxaliplatin, Paclitaxel, Panitumab, Pemetrexed, Rituximab, Tafluposide, Teniposide, Tioguanine, Topotecan, Tretinoin, Valrubicin, Vemurafenib, Vinblastine, Vincristine, Vindesine, Vinorelbine, Vorinostat, Romidepsin, 5-fluorouracil (5-FU), 6-mercaptopurine (6-MP), Cladribine, Clofarabine, Floxuridine, Fludarabine, Pentostatin, Mitomycin, ixabepilone, Estramustine, prednisone, methylprednisolone, dexamethasone or a combination thereof.

Still in accordance with the present invention, the hybrid polymerized liposomal nanoparticle comprises a targeting agent conjugated to its surface. In various embodiments, the targeting agent can be diabodies, antibodies, ligands, proteins, peptides, carbohydrates, vitamins, nucleic acids and combinations thereof. In various embodiments, the targeting agent is an anti-CD19 antibody, anti-CD34 antibody, anti-CD99 antibody, anti-CD117 antibody, anti-CD166 antibody, or anti-CA19-9 antibody, or a combination thereof. In various embodiments, the targeting agent is a peptide capable of specifically binding to a cell surface molecule. In accordance with the present invention, the cell surface molecule can be a cell membrane protein selected from the group consisting of structural proteins, cell adhesion molecules, membrane receptors, carrier proteins and channel proteins. Examples of the cell surface molecule include but are not limited to Activated Leukocyte Adhesion Molecule (CD-166), carbohydrate antigen 19-9 (CA19-9), Alphafetoprotein (AFP), Carcinoembryonic antigen (CEA), Ovarian cancer antigen (CA-125), breast cancer antigens (MUC-1 and epithelial tumor antigen (ETA)), Tyrosinase malignant melanoma antigen and Melanoma-associated antigen (MAGE), abnormal antigenic products of ras, p53, Ewing sarcoma antigen (CD-19), leukemia antigens (CD-99 and CD-117), Vascular Endothelial Growth Factor (VEGF), Epithelial Growth Factor Receptor (EGFR), Her2/neu, or prostate-specific membrane antigen (PSMA).

In various embodiments, the hybrid polymerized liposomal nanoparticle is administered once, twice, three or more times. In various embodiments, the hybrid polymerized liposomal nanoparticle is administered 1-3 times per day, 1-7 times per week, or 1-9 times per month. In various embodiments, the hybrid polymerized liposomal nanoparticle is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years.

In various embodiments, the hybrid polymerized liposomal nanoparticle is administered to deliver the therapeutic agent at about 0.001 to 0.01, 0.01 to 0.1, 0.1 to 0.5, 0.5 to 5, 5 to 10, 10 to 20, 20 to 50, 50 to 100, 100 to 200, 200 to 300, 300 to 400, 400 to 500, 500 to 600, 600 to 700, 700 to 800, 800 to 900, or 900 to 1000 mg per kg body weight of the subject. In various embodiments, the hybrid polymerized liposomal nanoparticle is administered to deliver the therapeutic agent at about 0.001 to 0.01, 0.01 to 0.1, 0.1 to 0.5, 0.5 to 5, 5 to 10, 10 to 20, 20 to 50, 50 to 100, 100 to 200, 200 to 300, 300 to 400, 400 to 500, 500 to 600, 600 to 700, 700 to 800, 800 to 900, or 900 to 1000 mg per m2 body surface area of the subject. In one embodiment, the therapeutic agent is doxorubicin, or a functional equivalent, analog, derivative or salt of doxorubicin. In certain embodiments, the therapeutic agent is administered to a human.

Typical dosages of an effective amount of the therapeutic agent can be in the ranges recommended by the manufacturer where known therapeutic compounds are used, and also as indicated to the skilled artisan by the in vitro responses in cells or in vivo responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models. In various embodiments, the polymerized liposomal nanoparticle may be administered once a day (SID/QD), twice a day (BID), three times a day (TID), four times a day (QID), or more, so as to administer an effective amount of therapeutic agent to the subject, where the effective amount is any one or more of the doses described herein.

In some embodiments, the hybrid polymerized liposomal nanoparticle may be administered at the prevention stage of a condition (i.e., when the subject has not developed the condition but is likely to or in the process to develop the condition). In other embodiments, the hybrid polymerized liposomal nanoparticle may be administered at the treatment stage of a condition (i.e., when the subject has already developed the condition). As a non-limiting example, the target condition is a cancer.

In accordance with the invention, the hybrid polymerized liposomal nanoparticle may be administered using the appropriate modes of administration, for instance, the modes of administration recommended by the manufacturer. In accordance with the invention, various routes may be utilized to administer the hybrid polymerized liposomal nanoparticle of the claimed methods, including but not limited to aerosol, nasal, oral, transmucosal, transdermal, parenteral, implantable pump, continuous infusion, topical application, capsules and/or injections. In various embodiments, the hybrid polymerized liposomal nanoparticle is administered intravascularly, intravenously, intraarterially, intratumorally, intramuscularly, subcutaneously, intranasally, intraperitoneally, or orally.

Pharmaceutical Compositions

The present invention also provides the hybrid polymerized liposomal nanoparticle described herein in the form of various pharmaceutical formulations. These pharmaceutical compositions may be used for treating, preventing, reducing the likelihood of having, reducing the severity of and/or slowing the progression of a condition in a subject. In accordance with the invention, the condition can be a cancer. In certain embodiments, the condition is leukemia or sarcoma.

In one embodiment, the present invention provides a pharmaceutical composition comprising a hybrid polymerized liposomal nanoparticle described herein. In another embodiment, the present invention provides a pharmaceutical composition comprising two or more hybrid polymerized liposomal nanoparticles described herein. In still another embodiment, the present invention provides a pharmaceutical composition comprising a plurality of hybrid polymerized liposomal nanoparticles described herein. In accordance with the present invention, the hybrid polymerized liposomal nanoparticle comprises a therapeutic agent loaded therein and/or a targeting agent conjugated thereto. Preferred pharmaceutical compositions also exhibit minimal toxicity when administered to a mammal.

In various embodiments, the pharmaceutical compositions according to the invention can contain any pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal, parenteral, enteral, topical or local. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the parenteral route, the compositions may be in the form of solutions or suspensions for infusion or for injection. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Typically, the compositions are administered by injection. Methods for these administrations are known to one skilled in the art. In certain embodiments, the pharmaceutical composition is formulated for intravascular, intravenous, intraarterial, intratumoral, intramuscular, subcutaneous, intranasal, intraperitoneal, or oral administration.

In various embodiments, the pharmaceutical composition is administered once, twice, three or more times. In various embodiments, the pharmaceutical composition is administered 1-3 times per day, 1-7 times per week, or 1-9 times per month. In various embodiments, the pharmaceutical composition is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. In various embodiments, the pharmaceutical composition may be administered once a day (SID/QD), twice a day (BID), three times a day (TID), four times a day (QID), or more, so as to administer an effective amount of the therapeutic agent to the subject, where the effective amount is any one or more of the doses described herein or known to one of ordinary skill in the art.

In various embodiments, the pharmaceutical compositions according to the invention can contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Before administration to patients, formulants may be added to the composition. A liquid formulation may be preferred. For example, these formulants may include oils, polymers, vitamins, carbohydrates, amino acids, salts, buffers, albumin, surfactants, bulking agents or combinations thereof.

Carbohydrate formulants include sugar or sugar alcohols such as monosaccharides, disaccharides, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof. "Sugar alcohol" is defined as a C4 to C8 hydrocarbon having an —OH group and includes galactitol, inositol, mannitol, xylitol, sorbitol, glycerol, and arabitol. These sugars or sugar alcohols mentioned above may be used individually or in combination. There is no fixed limit to amount used as long as the sugar or sugar alcohol is soluble in the aqueous preparation. In one embodiment, the sugar or sugar alcohol concentration is between 1.0 w/v % and 7.0 w/v %, more preferable between 2.0 and 6.0 w/v %.

Amino acids formulants include levorotary (L) forms of carnitine, arginine, and betaine; however, other amino acids may be added.

In some embodiments, polymers as formulants include polyvinylpyrrolidone (PVP) with an average molecular weight between 2,000 and 3,000, or polyethylene glycol (PEG) with an average molecular weight between 3,000 and 5,000.

It is also preferred to use a buffer in the composition to minimize pH changes in the solution before lyophilization or after reconstitution. Most any physiological buffer may be used including but not limited to citrate, phosphate, succinate, and glutamate buffers or mixtures thereof. In some embodiments, the concentration is from 0.01 to 0.3 molar. Surfactants that can be added to the formulation are shown in EP Nos. 270,799 and 268,110.

Another drug delivery system for increasing circulatory half-life is the liposome. Methods of preparing liposome delivery systems are discussed in Gabizon et al., Cancer Research (1982) 42:4734; Cafiso, Biochem Biophys Acta (1981) 649:129; and Szoka, Ann Rev Biophys Eng (1980) 9:467. Other drug delivery systems are known in the art and are described in, e.g., Poznansky et al., DRUG DELIVERY SYSTEMS (R. L. Juliano, ed., Oxford, N.Y. 1980), pp. 253-315; M. L. Poznansky, Pharm Revs (1984) 36:277.

After the liquid pharmaceutical composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is administered to subjects using those methods that are known to those skilled in the art.

The compositions of the invention may be sterilized by conventional, well-known sterilization techniques. The resulting solutions may be packaged for use or filtered under aseptic conditions and lyophilized, the lyophilized preparation being combined with a sterile solution prior to administration. The compositions may contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and stabilizers (e.g., 1-20% maltose, etc.).

Kits of the Invention

In various embodiments, the present invention provides a kit for treating, preventing, reducing the severity of and/or slowing the progression of a condition in a subject. The kit comprises: a quantify of a hybrid polymerized liposomal nanoparticle described herein; and instructions for using the hybrid polymerized liposomal nanoparticle to treat, prevent, reduce the severity of and/or slow the progression of the condition in the subject. In accordance with the present invention, the hybrid polymerized liposomal nanoparticle comprises a therapeutic agent loaded therein and/or a targeting agent conjugated thereto.

The kit is an assemblage of materials or components, including at least one of the inventive compositions. The exact nature of the components configured in the inventive kit depends on its intended purpose. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to affect a desired outcome. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a glass vial used to contain suitable quantities of a composition as described herein. The packaging material generally has an external label which indicates the contents and/or purpose of the kit and/or its components.

EXAMPLES

The following examples are offered for illustrative purposes only, and are not intended to limit the scope of the present invention in any way.

Example 1: Hybrid Polymerized Liposomal Nanoparticle (HPLN) for Targeted Drug Delivery The HPLN delivery system being proposed here is illustrated in FIG. 1A-FIG. 1D. These nanoparticles can be synthesized to nearly any size and composition, within a broad range. They mimic conventional liposomes or even normal cell membranes, but with important differences: the wall can be cross-linked to any degree desired, preventing loss of contents over time, and allowing active loading via an ion gradient of a given cytotoxic agent to concentrations that result in crystallization of the agent within the nanoparticle (Federman et al. "Enhanced Growth Inhibition of Osteosarcoma by Cytotoxic Polymerized Liposomal Nanoparticles Targeting the Alcam Cell Surface Receptor", Sarcoma, 2012, 126906). Most importantly, the surface of the particle can be modified at will to covalently label with a targeting agent of nearly any kind. Our approach is focused on improving tumor killing by use of very high concentrations of conventional agents delivered selectively to leukemia or sarcoma cells, although future iterations will allow targeting to many different types of tumor cells.

By including a significant amount of (non-polymerizable) phospholipid (hydrogenated soy PC) in to the polymerizable lipid, a new hybrid-PLN, "HPLN", was produced. Below is a non-limiting example of HPLN preparation. HPLNs were prepared from h-PEG1PCDA, hydrogenated soy PC, cholesterol and m-PEG2000-DSPE and m-PEG2000-PCDA at a molar proportion of 14:51:32:2:1, according to the method previously described (Bruehl et al., "Polymerized liposome assemblies: bifunctional macromolecular selectin inhibitors mimicking physiological selectin ligands," Biochemistry, vol. 40, no. 20, pp. 5964-5974, 2001). Briefly, lipids were mixed and evaporated in vacuo, to a film. 155 mM ammonium sulfate was added to the films so as to give a 15 mM (total lipid and chloesterol) suspension. The suspension was heated in a bath sonicater to 65-80° C. 30 min. The resulting milky solution was then extruded through stacked polycarbonate membranes (80 nm), ten times, with a homogenizer/extruder (C5, Avestin, Inc., Ottawa, ON, Canada), heated to about 75° C. The nearly clear liposome solutions were cooled to 5° C. for 12 hours. After warming to ambient temperature, the liposomes were polymerized by UV light irradiation (254 nm) with a Spectrolinker XL-1000 UV Crosslinker (Spectronics Corp.) for 1 minute. The resulting blue HPLNs were heated to 65° C. for 5 min to convert them to the red (fluorescent) form. The colored solutions were syringe filtered through 0.2 um cellulose acetate filters in order to remove trace insoluble contaminants.

Figure 1B:
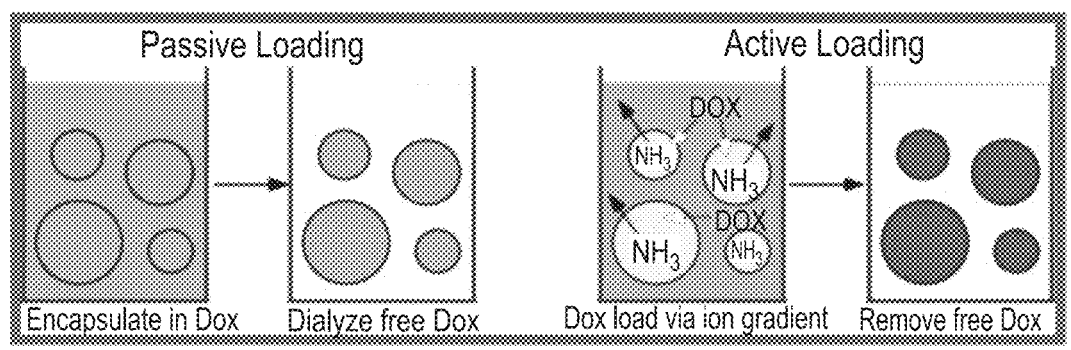
Figure 1C:
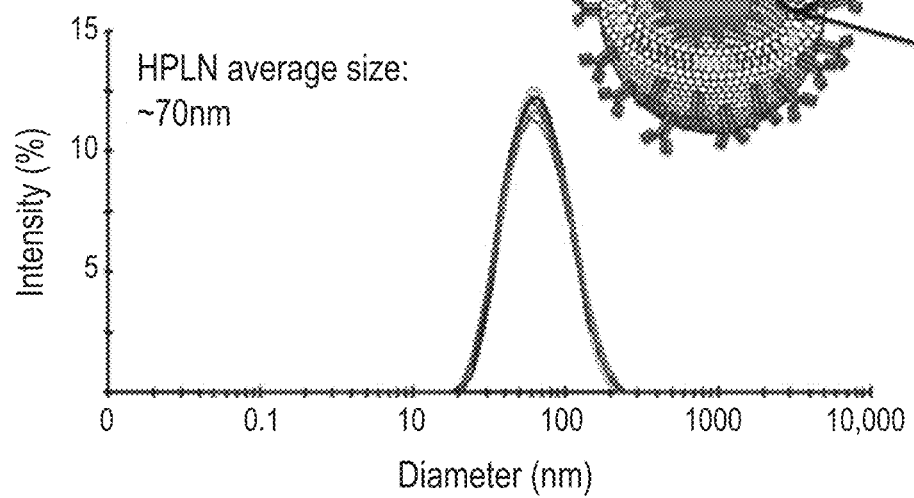
Figure 1D:
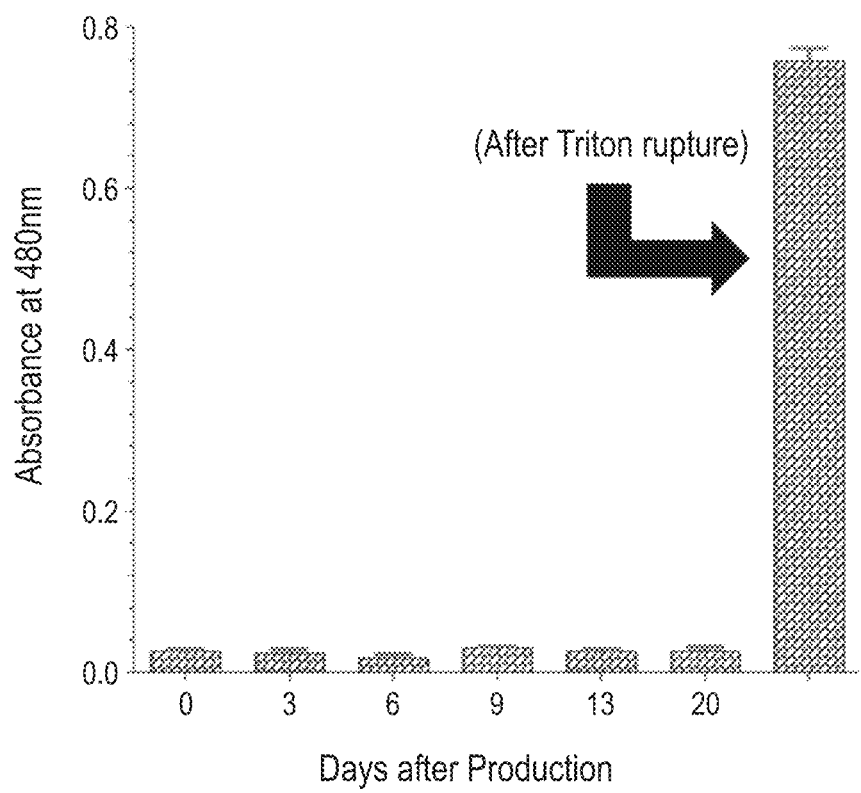

To produce doxorucibin loaded HPLNs the ammonium sulfate-containing HPLN were passed over a G50 Sepharose column (washed with 1×PBS) to exchange the external buffer. The liposomes were then incubated with Doxorubicin-HCl (Shandong Tianyu Fine Chemical Co., Ltd.) at a concentration of 1 mg of dox to 2 mg of HPLN while heating to 60° C. for 40 min. (FIG. 1B, active loading). The unencapsulated doxorubicin was removed by passing the solution over a G50 Sepharose column (washed with 1×PBS). The average particle size measurements were obtained on a Zetasizer Nano-S (Malvern Inst.), in a solution of 10 mM sodium chloride (FIG. 1C).

To obtain antibody-labeled micelles, antibodies were partially reduced to expose free thiol groups, followed by incubated with micelles composed of m-PEG2000-DSPE and maleimide-PEG2000-DSPE (in a molar ratio of 4:1), and purified by passing the solution over a Sepharose CL-4B column (washed with 1×PBS). To produce antibody-targeted HPLNs, the dox (or dox free) HPLN solutions were incubated with antibody-labeled micelles, for 24 hrs. The excess micelle was removed by passing the solution over a Sepharose CL-4B column (washed with 1×PBS) to yield antibody-targeted HPLNs.

Alternatively, mal-HPLNs were prepared from h-PEG1PCDA, hydrogenated soy PC, cholesterol and m-PEG2000-DSPE, mal-PEG2000-DSPE and m-PEG2000-PCDA at a molar proportion of 14:48:32:2:3:1, according to the method previously described (Bruehl et al., "Polymerized liposome assemblies: bifunctional macromolecular selectin inhibitors mimicking physiological selectin ligands," Biochemistry, vol. 40, no. 20, pp. 5964-5974, 2001). Briefly, lipids were mixed and evaporated in vacuo, to a film. 155 mM ammonium sulfate was added to the films so as to give a 15 mM (total lipid and cholesterol) suspension. The suspension was heated in a bath sonicater to 65-80° C. 30 min. The resulting milky solution was then extruded through stacked polycarbonate membranes (80 nm), ten times, with a homogenizer/extruder (C5, Avestin, Inc., Ottawa, ON, Canada), heated to about 65° C. The nearly clear liposome solutions were cooled to 5° C. for 12 hours. After warming to ambient temperature, the liposomes were polymerized by UV light irradiation (254 nm) with a Spectrolinker XL-1000 UV Crosslinker (Spectronics Corp.) for 1 minute. The resulting blue HPLNs were heated to 65° C. for 5 min to convert them to the red (fluorescent) form. The colored solutions were syringe filtered through 0.2 um cellulose acetate filters in order to remove trace insoluble contaminants.

To produce doxorucibin loaded mal-HPLNs the ammonium sulfate-containing HPLN were passed over a G50 Sepharose column (washed with 1×PBS) to exchange the external buffer. The liposomes were then incubated with Doxorubicin-HCl (Shandong Tianyu Fine Chemical Co., Ltd.) at a concentration of 1 mg of dox to 2 mg of HPLN while heating to 60° C. for 40 min. The unencapsulated doxorubicin was removed by passing the solution over a G50 Sepharose column (washed with 1×PBS). The average particle size measurements were obtained on a Zetasizer Nano-S (Malvern Inst.), in a solution of 10 mM sodium chloride.

To produce antibody-targeted HPLNs, the dox (or dox free) mal-HPLN solutions were incubated with antibody (partially reduced to expose free thiol groups) for 24 hours and purified by passing the solution over a Sepharose CL-4B column (washed with 1×PBS).

Example 2

We specifically tested HPLN nanoparticle enabled targeted cancer therapy for leukemia. We provide a novel, nanoscale technology to treat relapsed and refractory cancer patients. A targeted, delivery vehicle can successfully treat a mouse xenograft of human treatment-resistant leukemia. We synthesized antibody-labeled nanoparticles utilizing a single type of tumor-specific targeting ligand (CD-19 or CD-117 antibodies, Fab fragments or diabodies) with payloads including conventional cytotoxics (vincristine or doxorubicin); validated tumor cell targeting using established in vivo methods for adult leukemia, in a mouse model; assessed systemic toxicity by sequential serum chemistry followed by necropsy; and conducted a DMET type study at low dose for ALL and/or AML mice. We examined the clinical translational potential of the optimized HPLNs by documenting the systemic delivery and tumor uptake, as well as confirming tumor localization of the HPLNs.

Table 1 shows that that presentation of the human antibody to CD-19 on HPLNs facilitates strong binding recognition of the nanoparticles to CD-19 expressing cells; the non-specific cell binding to CD-19 negative cells is very low (similar to the no antibody control HPLNs) and; this confirms that freshly isolated ALL leukemia cells from human patients (CHLA3 and US7R) are susceptible to strong positive recognition by the newly created anti-hCD-19/HPLNs.

TABLE 1 specific binding of the human antiCD19 antibody conjugated HPLN to various cells.

| Cells | CD-19 | Characteristics or source | hCD-19/HPLN | HPLN |
|---|---|---|---|---|
| RAJI | (+) | Burkitt Lymphoma | 99.54 | 0.88 |
| REH | (+) | ALL (B-Lymphocytes), pre-B leukemia | 99.7 | 0.37 |
| 697 | (+) | ALL (TEL-Jak2) | 99.88 | 0.87 |
| BEL-1 | (+) | ALL (MLL-AF4) | 99.68 | 0.09 |
| CHLA3 | (+) | ALL (Patients), pre-B leukemia | 84.92 | 0.39 |
| US7R | (+) | ALL (Patients), pre-B leukemia | 99.18 | 0.51 |
| TC32 | (−) | Ewing sarcoma | 0.51 | 0.35 |
| Molt-T | (−) | ALL (T-Lymphocytes) | 0.46 | 0.45 |
| K562 | (−) | CML (BCRL-ABL) | 0.15 | 0.14 |

I. Construction of a Targeted, Drug-Loaded Hybrid Polymerized Liposomal Nanoparticle Formulation Optimization:

We recognized that for this approach to be successful it is key to deliver a high dose of cytotoxic drug to the tumor cell so that only a very small number of nanoparticles are required to attach themselves, become internalized and kill the cell. Therefore we endeavored to encapsulate the maximum possible level of drug concentration in the PLN. Through active loading much higher amounts of drug could be incorporated into liposomes, compared to passive loading (Haran, 1993). Active loading employs a method of establishing a low pH sink ("pH gradient") inside the liposome wherein an amine-bearing drug like doxorubicin crosses the membrane to neutralize the acidic interior. The drug freely flows into the liposome to such a large extent that it crystalizes in the interior. To employ the published pH gradient active doxorubicin loading strategy (Haran, 1993)

with the PLNs, we needed to adjust the lipid formulation in the nanoparticle. Compared to conventional stealth liposomes (e.g. "Doxil™"), our original fully polymerized PLN formulation showed only a fraction of doxorubicin could be loaded, even after prolonged incubation times and higher applied temperatures. Through reformulation, by including a significant amount of (non-crosslinkable or non-polyermizable) phospholipid (hydrogenated soy PC), a hybrid-PLN, "HPLN", was produced. Further, the polymerizable lipid portion is modified to generate a new HPLN; i.e. a polymerizable lipid having a PEG chain (e.g., m-PEG2000-PCDA) is mixed with a polymerizable lipid having no PEG chain (e.g., h-PEG1-PCDA).

Now levels of doxorubicin could be incorporated into the HPLN, similar to those reported for Doxil (0.15 vs. 0.16 umol Dox/umol liposome components, respectively). The key innovation was reformulating the lipid-based nanoparticle to contain a lower amount of photopolymerizable diacetylene lipid while still resulting in a robust polymerization upon UV irradiation. We found that the loading of drug into HPLNs was about 10-fold higher, compared to the fully polymerized PLN liposomes (Federman, 2012). To complete the mouse studies, we prepared 500 mg of HPLN/Dox and approximately 20 mg of CD-19 monoclonal (targeting) antibody.

Preparation of Antibody Targeted, Drug Loaded Nanoparticles:

The final HPLN/Dox particles were prepared by conjugating monoclonal antibodies that target the nanoparticle to the CD-19 cell surface marker on ALL-type human leukemia cells (REH cells). Chemically reduced anti-CD-19 antibodies were conjugated to micelles composed of maleimide-terminated and methoxy-terminated Peg2000 phospholipids (Iden 2001). Upon exposure of the antibody-labeled micelles to pre-formed HPLN/Dox nanoparticles, an insertion process of micelle lipids into the HPLN membrane spontaneously occurs, yielding anti-CD-19/HPLN/Dox particles. The targeted particles were purified by size exclusion filtration to remove unconjugated antibodies and other small, molecular weight impurities.

II. Validation of Tumor Cell Targeting Using Established In Vivo Methods for Adult Leukemia, in a Mouse Model Mouse Treatments:

To complete the mouse efficacy and safety studies we injected NOG mice with $6 \times 10^6$ luciferase transfected human Acute Lymphoblastic Leukemia (REH cells). This special transgenic type of mouse has deletions in the gene encoding the interleukin 2 receptor γ (IL2Rγ) and has added genes expressing human iL3, GM-CSF and SCF. To prevent rejection of injected human leukemia cells, the NOG mice have a complete lack of B, T, and NK cells, and a deficiency of cytokine signaling. The mice were separated into six groups. Group 1 received only buffer treatment; group 2-untargeted, unloaded HPLN; group 3-untargeted, HPLN/Dox (2 mg Dox/kg); group 4- (targeted) anti-CD-19/HPLN/Dox (2 mg Dox/kg); group 5-Doxil (2 mg Dox/kg); and group 6- (free) doxorubicin (2 mg Dox/kg).

Upon injection of the leukemia cells, Xenogen camera images were done once per week and used to assess both tumor cell distribution and quantitative tumor burden. After 10 days post leukemia cell injection, our targeted nanoparticle drug (anti-CD-19/HPLN/Dox) or control particles or drugs, were administered to the mice, in once a week dosages. The amount of drug given was based on the active substance (doxorubicin), not on total nanoparticle mass in each formulation (except for group 2, these mice received an equivalent HPLN dose in unloaded form).

Figure 4:
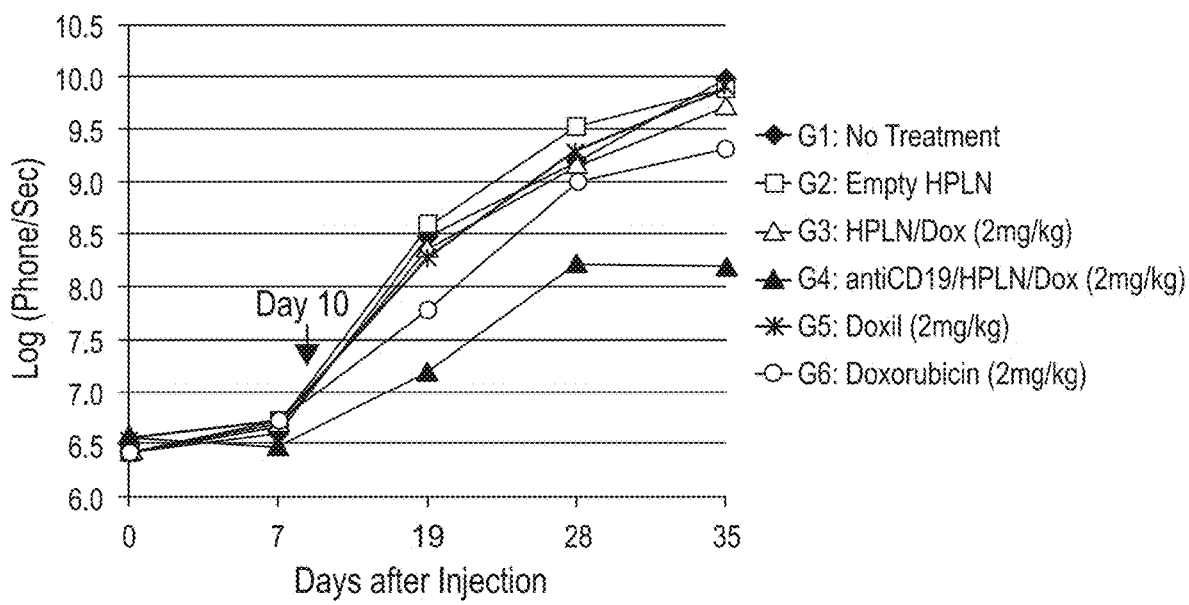
FIG. 4 depicts, in accordance with various embodiments of the invention, relative tumor growth as measured by Xenogen camera. Starting at day 10 after REH-Luc leukemia tumor cell implantation mice in Group 1 received only buffer treatment by IV administration; group 2-untargeted, HPLN; group 3-untargeted, HPLN/Dox (2 mg Dox/kg); group 4-(targeted) anti-CD-19/HPLN/Dox (2 mg Dox/kg); group 5-Doxil (2 mg Dox/kg); and group 6-doxorubicin (2 mg Dox/kg). This data is a compilation of the results from several different sequential studies.

Efficacy Results:

The HPLNs and drug-loaded HPLNs were very well tolerated in the mice, as there were no acute toxic reactions observed. This was not the case for animals in the group 6, receiving free doxorubicin. They were observed to lose weight and appeared sickly as a result of the drug treatment. The treated mice in groups 2, 3 and group 5 showed a steady tumor growth progression, similar to the untreated mice in group 1 (FIG. 4). Only the mice treated with the anti-CD-19/HPLN/Dox (group 4) or free drug (group 6) showed a significant tumor reduction. At day 35, there was almost a two-log difference for the anti-CD-19/HPLN/Dox (group 4) and about a three quarter log difference for the Doxil (group 6) animals, compared to the controls (FIG. 4).

We wished to determine if a higher weekly dose of targeted anti-CD-19/HPLN/Dox would result in a greater reduction in tumor burden, compared to control. The next study we undertook compared only anti-CD-19/HPLN/Dox and the non-treated control animals. Here again $6 \times 10^6$ REH cells were administered to mice and a dose of 2 mg/kg Dox in the targeted nanoparticles was administered either once or twice per week (twice per week is double the weekly dosage from the previous study).

The Xenogen images at day 28 clearly show that the tumor size and burden are markedly reduced in the twice-per-week administration compared to no treatment control or the once-per-week dosing (FIG. 5 and FIG. 9A-FIG. 9B). We calculated from the Xenogen tumor image dosimetry that twice weekly versus once weekly dosing resulted in a 2.5 log reduction in tumor burden.

III. Assessing Systemic Toxicity

Figure 6:
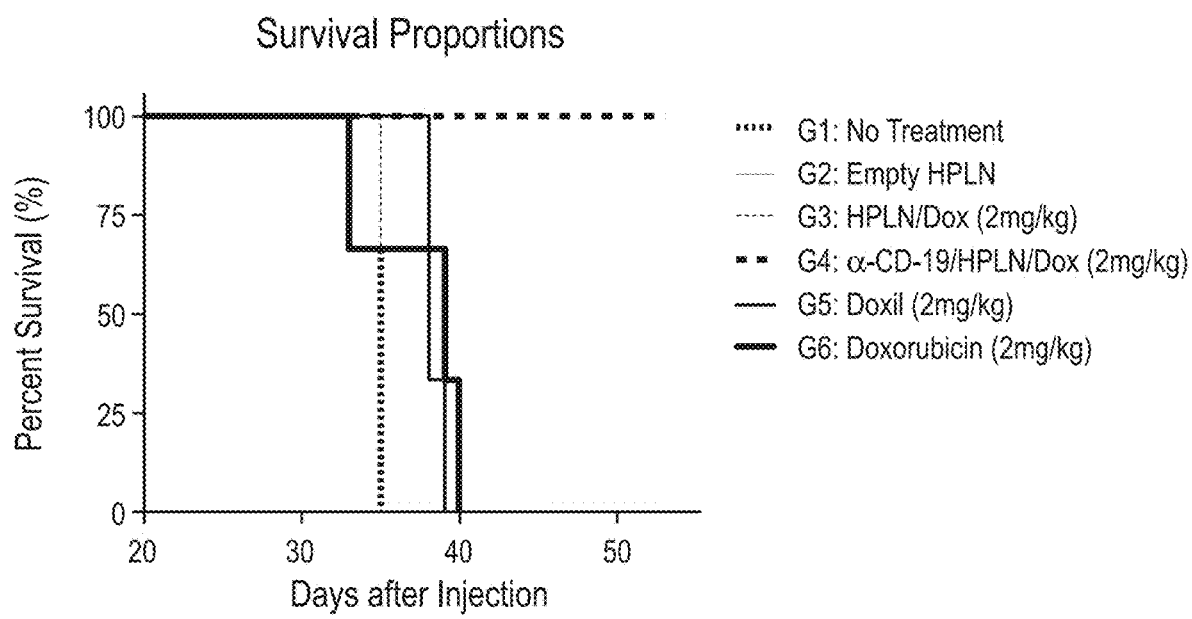
FIG. 6 depicts, in accordance with various embodiments of the invention, survival curve for REH leukemia tumor bearing mice treated in groups 1-6. Group 1 received only buffer treatment; group 2-untargeted, HPLN; group 3-untargeted, HPLN/Dox (2 mg Dox/kg); group 4- (targeted) anti-CD-19/HPLN/Dox (2 mg Dox/kg); group 5-Doxil (2 mg Dox/kg); and group 6-doxorubicin (2 mg Dox/kg).

Mouse Survival:

The mice in the earlier (once-per-week dosing) study were examined out to day 50 for survival. Even though the mice in groups 4 and 6 showed reduction in tumor burden, the treatment of the free drug doxorubicin (group 6) induced severe side effects that resulted in the weight loss and an unhealthy appearance (reduced weighed, slow mobility, hair loss) of these animals. This off-target toxicity was not observed for group 4 (2 mg/kg Dox in anti-CD-19/HPLN/Dox) and 100% of these animals appeared healthy and survived out to terminal sacrifice at day 50 (FIG. 6).

Figure 7:
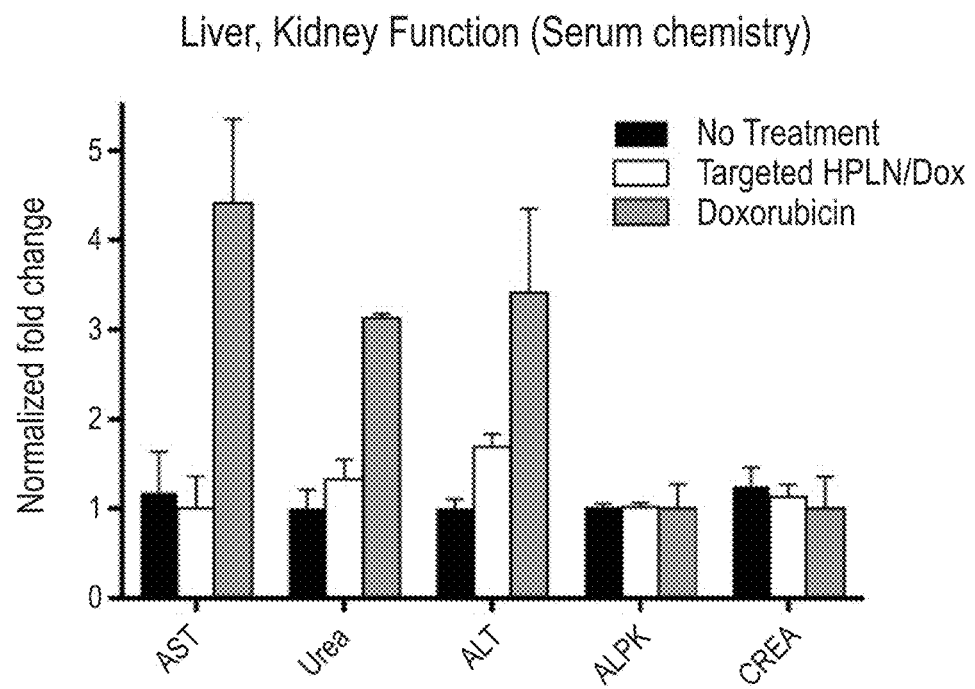
FIG. 7 depicts, in accordance with various embodiments of the invention, comparison of the liver and kidney enzyme function between untreated control, (targeted) anti-CD-19 doxorubicin loaded HPLN treated, and free doxorubicin treated animals. The treated animals were given the highest dose tested, 2.0 mg/kg doxorubicin two times per week.
Figure 8:
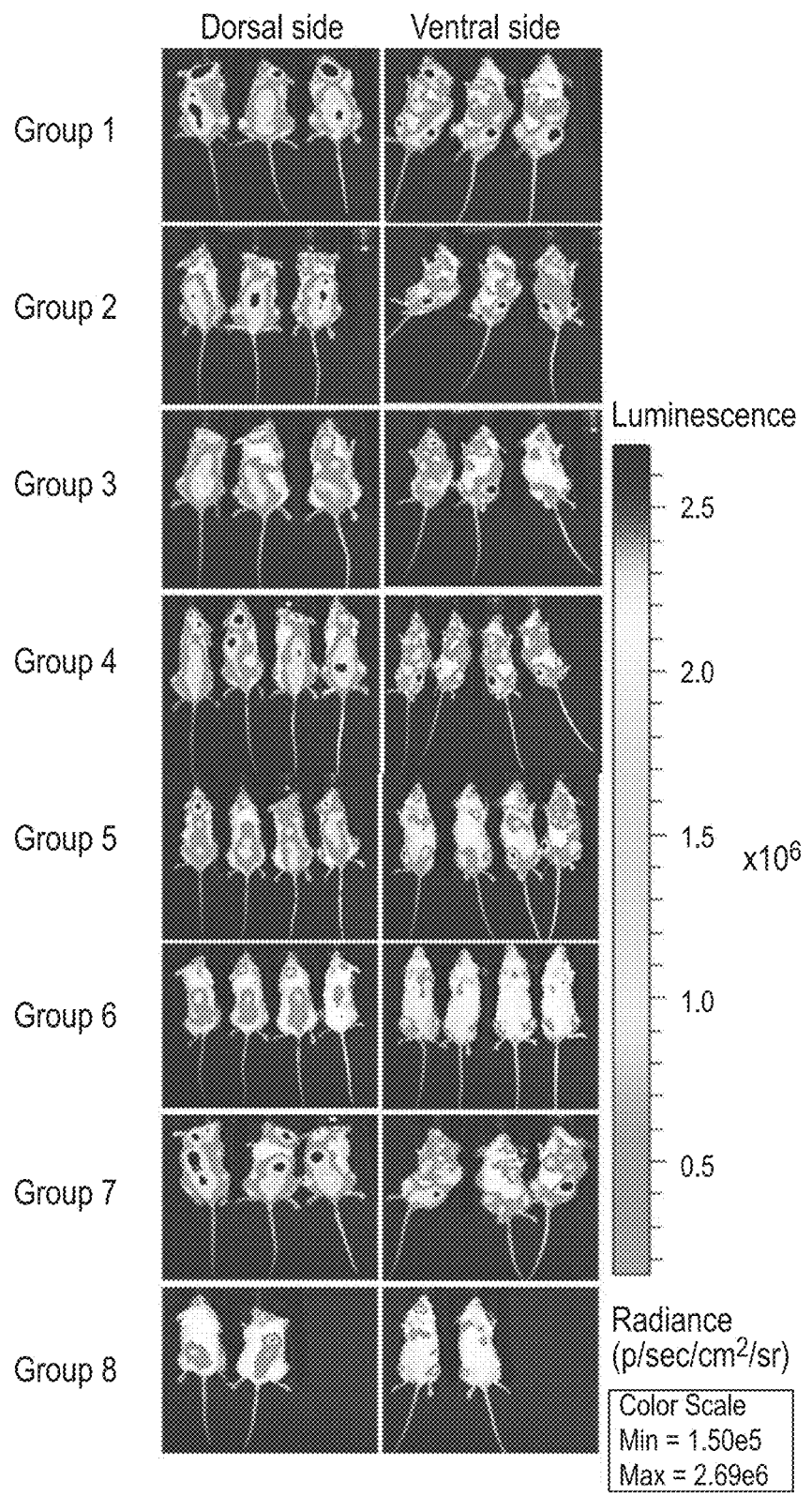
FIG. 8 depicts, in accordance with various embodiments of the invention, Xenogen camera images of treated and untreated mice bearing REH-Luc leukemia tumor xenografts at day 35. Color bar from red (biggest tumor mass) to purple (smallest tumor mass) gives a relative tumor size comparison. The mice were separated into eight groups. Group 1 received only buffer treatment; group 2-untargeted, low dose HPLN/Dox (1 mg Dox/kg); group 3-untargeted, higher dose HPLN/Dox (2 mg Dox/kg); group 4-low dose anti-CD-19/HPLN/Dox (0.5 mg Dox/kg); group 5-medium dose anti-CD-19/HPLN/Dox (1 mg Dox/kg); group 6-higher dose anti-CD-19/HPLN/Dox (2 mg Dox/kg); group 7-Doxil (2 mg Dox/kg); and group 8-doxorubicin (2 mg Dox/kg). The tumor size and burden is markedly less in groups 6 and 8.

Serum Chemistry Toxicity Results:

Analysis of the clinical chemistry tests after 4 weeks, with twice-weekly treatment of anti-CD-19-HPLN-Dox at 2.0 mg Dox/kg, showed minor but insignificant changes in liver and kidney function (FIG. 7). For creatinine, AST and ALT the values for the treated animals were within the margin of error of the untreated control animals. There was a slight increase in urea nitrogen noted in the treated animals, but this change is not considered significant.

Figure 3:
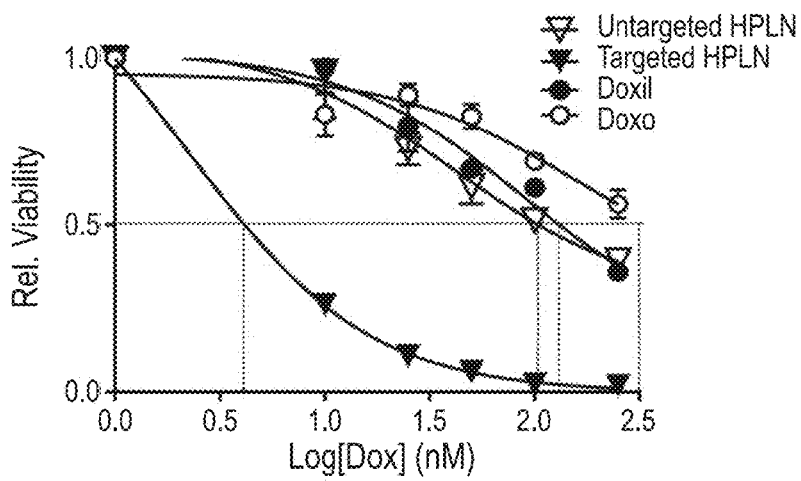
FIG. 3 depicts, in accordance with various embodiments of the invention, cytotoxicity IC50s for untargeted HPLN-Dox, Targeted HPLN-Dox, Doxil and free Doxorubicin "Doxo". Different forms of HPLNs, Doxil and free Doxorubicin were incubated with Ewing sarcoma cells (TC32). Mean IC50 shows that targeted HPLNs have a 20-fold increase and 40-fold in cytotoxicity over untargeted HPLN and Doxil, respectively.

The unexpected superior efficacy of the simple (untargeted) HPLN/Dox formulation over the conventional (untargeted) liposomal doxorubicin formulation (Doxil™) in cell culture makes this HPLN drug delivery approach compelling since the encapsulated drug seems to be more bioavailable to the tumor cells in the HPLN form (FIG. 3). The inclusion of a tumor cell-targeting agent increases the tumor-killing efficacy another 10-12 fold in vitro. In transgenic mice bearing human leukemia cells, the only mice to survive and appear healthy (out to terminal sacrifice at day 50) were those receiving a 2 mg/kg doxorubicin dose in anti-CD-19/HPLN/Dox nanoparticles. This survival response was accompanied by a nearly 2-log measured reduction in tumor burden for once per week dosing. By simply doubling the weekly dose of anti-CD-19/HPLN/Dox, the tumor burden is reduced about 2.5-logs, without any noticeable increase in off-target toxicity. Analysis of liver enzyme function and kidney function in the animals receiving the highest HPLN/Dox dose showed no significant change in these values compared to untreated control animals. Additional studies have shown that polydiacetylene-containing nanoparticles show little or no cytotoxicity to normal tissues and are minimally immunogenic. All of these data taken together strongly suggest that the HPLN may serve as a very important drug delivery vehicle to treat human adult leukemia, and other malignancies.

Example 3: Demonstrate HPLN Targeting to Cancer Cells with a New, Synthetic Peptide Affinity Agent We employed monoclonal antibodies (anti-CD-19) that bind HPLNs selectively to human ALL tumor cells. Because the targeting antibodies are of mouse origin, immunological recognition of the foreign proteins may be problematic with repeated dosing, when administered to human patients. Thus, we develop and use high-affinity, highly stable peptide affinity agents. A peptide-based affinity agent that bypasses the use of non-human mouse monoclonal antibodies significantly improves this new, targeted therapy for initial use in poor prognosis, relapsed cancer patients.

Typically the engineered peptide agents that are uncovered by screening phage display libraries of random peptide sequences against cells that express a unique tumor cell-surface receptor. A phage library is prescreened against a similar cell line that differs only by the lack of expression of the tumor receptor (negative cell line). In this way, phages that stick specifically or non-specifically to the negative cell line are removed from the library. The new, sublibrary is now passed against the positive cell line and any phages that bind are likely to stick as a result of specific recognition of the receptor. This approach will bind the target with very high affinity, with $K_i$'s approximately in the low nM range, similar to those of many of the best monoclonal antibodies. This design strategy for identification of engineered peptides is general and does not require specific structures (e.g., α-helices, β-sheets, turns) or even a priori knowledge of the structure in order to work. All of these features enable our efforts to create stable peptides that can replace the antibodies currently used to target HPLNs to leukemia cells.

Once a binding peptide sequence or sequences are isolated using the selection, we synthesize 2-3 of the top peptides for validation and incorporation into the nanoparticles. Nanoparticles are synthesized with cytotoxic drug payloads (doxorubicin) and purified to yield HPLN/Dox particles. Through lipid insertion methodology we incorporate the engineered affinity peptides by exposing the HPLN/Dox particles to peptide-labeled lipid micelles. We first evaluate tumor cell targeting using cultured human ALL cells (CD-19 and CD-117 positive) and human AML cells (CD-34 positive), and then validate the tumor killing in vivo, in a xenograft mice model injected with human leukemia ALL and AML cells.

Producing Pep-HPLNs:

Liposomal nanoparticles are synthesized via extrusion to give particles of narrow size distribution followed by active (pH gradient) loading with doxorubicin and final polymerization of the shell to produce HPLN/dox particles. We prepare peptide-terminated Peg lipids by incubating the thiol-containing peptide analogs with maleimide terminated Peg lipids (as demonstrated for the reduced monoclonal antibodies herein). These peptide-terminated Peg lipids are co-mixed with other methoxy-terminated Peg lipids to produce mixed micelles (Iden 2001). As was done with monoclonal antibody micelles, the peptide-terminated Peg lipid micelles are incubated with the HPLN/dox particles to insert the peptide lipids into the HPLN/dox particles, producing pep-HPLN/Dox.

Assaying Pep-HPLN/Dox for Tumor Targeting and Killing:

By using conventional diagnostic flow cytometry (FACS analysis) the peptide labeled HPLNs (pep-HPLN) are compared to the antibody labeled HPLNs for affinity binding to ALL cells and AML cells. Cells are exposed to the targeted HPLNs followed by a washing step to remove any unbound particles. FACS, utilizing the inherent fluorescence of the HPLN polymer, gives a good indication of the comparative efficacy of cell binding between the pep-HPLN compared to the anti-CD (-19, -117, -99 or -34)-HPLNs. After optimizing the per-particle level of targeting peptide, done by varying the HPLN/peptide-micelle ratio, both the in vitro binding assay and in vitro tumor killing study are undertaken to validate peptide-induced localization and uptake.

After the pep-HPLN is optimized to target CD-19, CD-117, CD-99 or CD-34 positive tumor cells, the in vivo tumorcidal activity assay in mice is performed. As before, NOG mice are injected with $6 \times 10^6$ luciferase transfected leukemia cells. The systemic distribution and cell killing by pep-HPLN/Dox are continuously assessed by eternal Xenogen camera imaging of the luciferase transfected leukemia cells. Follow-on studies after allowing established tumors to form, are subsequently conducted. In this way, the reduction in tumor burden by pep-HPLNs is analyzed for their therapeutic efficacy. This study leads to the successful identification of a synthetic peptide HPLN conjugate that can bind to leukemia cells at least as well as HPLNs targeted by the anti-CD-19, -99, -117 or -34 monoclonal antibodies, and provides a new formulation comprised of a drug-loaded, engineered peptide targeted HPLN (pep-HPLN/Dox) that functions in vivo with tumorcidal activity comparable to antibody targeted HPLN/Dox.

The tumor targeting of HPLNs by small, synthetic peptides may offer a powerful solution to avoiding the use of potentially immunogenic murine-derived antibodies in humans. In addition, we can turn toward more traditional methods for "humanizing" murine-derived monoclonal antibodies. Rational design approaches such as CDR grafting, "resurfacing", "superhumanization" or human string content optimization, and empirical methods using enrichment or high throughput selection will be considered (Almagro 2008). This could result in a molecule with minimal immunogenicity when applied to humans, while retaining the affinity and specificity of the murine antibody. Another approach is to use a human antibody phage display library. This commercially available technology is based on the rapid isolation of a fully human, cell-surface target-specific lead from a library of billions of distinct antibodies (www.dyax.com). By outsourcing the sequential panning of the commercial library of human-phage antibody constructs against the CD-19, CD-99, CD-117 and CD-34 proteins, high-affinity, high specificity human antibodies will be identified for attachment to HPLNs.

Example 4: Demonstrate Superior HPLN Targeting with Multiply Types of Targeting Agents on a Single Particle Using two or more targeting agents that match the high level of CDs identified on the ALL cells enhances the preferential HPLN affinity to leukemia cells and not to normal cells. Initially anti-CD-19 and anti-CD-117 are co-displayed on HPLN/dox particles and tested for binding and cytotoxicity. Also, we test HPLN/Dox formulations that co-display the small peptide targeting agents for CD-19 and CD-117 for binding and cytotoxicity. These features broaden the therapeutic efficacy verses systemic toxicity window in this HPLN drug delivery technology.

HPLN/Dox nanoparticles are treated with micelles containing two different antibody or peptide types. The affinity of the combination-targeting agent HPLN is empirically determined and optimized by evaluating tumor binding using adult leukemia cells in culture. A combination HPLN with superior binding affinity (compared to either single agent-HPLN) is identified, and the superior cell killing is confirmed in vitro followed by validating the superiority of tumorigenicity in vivo in the immunocompromised mouse model.

Preparing and Assaying Multi-Targeting Agent HPLN/Dox for Tumor Targeting and Killing:

The new targeting HPLNs are prepared and tested for cell binding and anti-tumor properties. Using the anti-CD-19 antibody and the anti-CD-117 antibody, micelles are prepared from each of these lipid-conjugated monoclonal antibodies. Also, the small peptide targeting agents for CD-19 and CD-117 are chemically conjugated to micelle-forming lipids as well. Again, through lipid insertion Ab or peptide labeled HPLNs are created. The ratio of Ab1 (or peptide1) type micelle to Ab2 (or peptide2) type micelle can be varied to lead to different relative levels of Ab1 and 2 (or peptide 1 and 2) on the same HPLN/dox particle. Affinity tumor binding is assayed by FACS analysis and the multi-targeting agent HPLN is compared to the single-agent labeled HPLNs. After optimizing the per-particle level and ratio of targeting agents the in vitro tumor killing is checked to assure that the combination of targeting agents is not detrimental to cell internalization and bioavailability of the cytotoxic drug. Finally, the optimized combination Ab- or pep-HPLN is tested in vivo for tumorcidal activity assay in mice. Again, the systemic distribution and cell killing by the multi-agent HPLNs are continuously assessed by external Xenogen camera imaging xenograft mice injected with luciferase transfected ALL cells. The reduction in tumor burden is quantitated and compared to control animals.

This study leads to the successful identification of a multi-targeting agent HPLN that displays at least 2-fold superior binding to leukemia cells, over the single agent targeted HPLNs, and provides a new, combination antibody or peptide targeted HPLN that functions in vivo with tumorcidal activity superior to the single agent targeted HPLN.

The targeting of HPLNs by a single targeting agent is a powerful way to selectively deliver drugs to tumor cells, and dual agent targeting may provide a significant boost in affinity and/or selectivity. Insuring that all the HPLNs have similar distributions of the dual agents may be difficult by just mixing the HPLNs with two populations of the different micelles. Depending upon the kinetics of lipid insertion, a particular particle might become enriched in one targeting agent and a heterogeneous population of multi-targeted HPLNs may result. This could potentially be avoided by attaching one targeting agent to the particle surface via active maleimide groups initially on the HPLN, then followed by lipid insertion of the second targeting agent. The dual agents might antagonize each other with regard to binding or cause retardation of internalization of the particle in the target cell, thereby leading to reduced drug efficacy. This could be ameliorated by adjusting the relative distribution of the dual targeting agents to promote internalization dominated by a single surface protein while still getting the added benefit of recognition of two different surface proteins from the initial binding event.

Example 5: Examine the Delivery of Multiple Therapeutic Agents in the Same HPLN or in a Cocktail of Different Single-Drug HLPNs We examine combination therapy with mixtures of cytotoxic drugs (doxorubicin, vincristine, irinotecan, cis-platin, cytarabine etc.) contained in the same HPLN. Alternatively, the same diversity of drugs are prepared as single drug agent HPLNs, but administered as admixtures of different HPLN drug types. The current therapy for adult leukemia (ALL) relies on a cocktail of vincristine, L-asparaginase, and dexamethasone or prednisone, with doxorubicin in any but favorable prognosis subsets. This combination of drugs is a high priority in the targeted HPLN formulations.

Targeted HPLNs containing selected small molecule cytotoxics will be prepared using methodology described herein for active drug loading and passive encapsulation when active loading is not applicable. In vitro testing is followed by in vivo assays with all HPLN drug combinations.

Preparing and Assaying Targeted, Multi-Drug Agent HPLNs:

The new targeting HPLNs are prepared and tested for cell binding and anti-tumor properties. The test drugs (doxorubicin, vincristine, topotecan, cis-platin, dexamethasone, cytarabine etc.) are obtained from commercial suppliers such as LC Laboratories, Sigma-Aldrich, Tocris and Desano Pharmaceuticals.

For both the cancer drugs topotecan and vincristine, active loading procedures into liposomes via pH gradient, have been published (Zucker 2010). This allows high concentrations to be established inside the HPLNs, similar to what we have obtained with doxorubicin. For the other test drugs, active liposome loading has not yet been described in the published literature. For these we establish as high an initial concentration as possible in the liposome formation buffer and passively encapsulate the drug upon initial particle assembly. The level of drug loading is determined by HPLN rupture and quantification by HPLC analysis. Each new drug is tested against ALL cells, first as a single agent in the CD-19 targeted HPLN in the in vitro tumor cell culture assay, then for each new anti-CD-19-HPLN/drug that shows promise a small number of combinations of these drugs are co-encapsulated, in as high a relative concentration as possible or in a ratio consistent with the currently used (non-encapsulated) cocktail. In vitro testing is again be used to determine if any of the combinations show superior efficacy with respect to tumor killing compared to equivalent doses of the single drug HPLNs. Combinations that mirror standard dosing induction protocols are created so as to allow targeted induction therapy that parallels standard induction therapy. The combination drug HPLN(s) showing improved efficacy for the amount of drug material encapsulated is administered to the xenograft mice, injected with human ALL tumors. The best drug combinations are tested again in the peptide targeted HPLNs, with possibly more than one targeting feature.

This study leads to the successful identification of a targeted, multi-drug containing HPLN that has superior efficacy with respect to ALL cells over the targeted, single drug agent HPLN, and provides a new, targeted multi-drug HPLN that functions in vivo with tumorcidal activity superior to the targeted, single drug agent HPLN.

While the targeted, single drug containing HPLN shows powerful efficacy both in the systemic and metastatic forms of leukemia, cocktails of drugs may push the window of off-target safety even wider. A potential drawback is that some combinations of drugs may be incompatible with each other or the HPLN lipids. This might be remedied by screening a wider array of drug combinations looking to identify those that seem chemically compatible while still synergizing each other's efficacy. If some combinations show promise but suffer from storage or stability problems, we can focus in on the approach where different drug combinations are co-administered in two (or more) different targeted HPLN populations. This variation may actually prove to be more advantageous as it will allow the different drugs to be administered at different times in the course of the chemotherapy, much like the existing induction protocols.

Example 6: HPLN Particle Parameter Optimization

Many of the in vivo pharmacokinetic/pharmacodynamic processes likely play a significant role in HPLN-delivered drug efficacy. We demonstrated that an HPLN formulation has good efficacy in the animal model. However, a fairly extensive matrix of HPLN particle parameters still exist for in vivo particle optimization. Without wishing to be bound by a particular theory, the following critical parameters can be optimized. (1) The percentage of polymer in the HPLN influences the efficacy of drug release and therefore tumor killing and also affects the particle toxicity toward normal cells. (2) The level of PEGylation influences HPLN circulation time and thereby tumor localization/uptake/killing kinetics. (3) The size of the HPLN affects efficacy in tumor localization and killing. (4) The per-particle amount of targeting agent affects the efficacy in tumor localization and killing.

To optimize the foregoing parameters, modifications to the formulation are conducted to vary the percentage of the polymer, vary the particle size and vary the amount of PEG and targeting molecules on the HPLNs. Preparing and characterizing the new targeting HPLNs, and testing cell binding and anti-tumor properties are carried out.

Polymer Content.

We have made the compelling observation that increasing the level of crosslinking lipid (h-PEG$_1$-PCDA) in the HPLN/dox formulation leads to increasing cytotoxicity toward cancer cells (Federman 2012). It is clear that this is not a toxicity arising from the lipid itself or in the polymeric form, since the PLNs without encapsulated cytotoxic drug shows very low toxicity toward normal cells. Without wishing to be bound by a particular theory, we think that the polymer modifies the nanoparticle membrane to facilitate release of the drug once inside the tumor cell, compared to conventional liposomes. Since increasing the amount of h-PEG$_1$-PCDA lipid leads to more highly polymerized HPLNs, we examine the effects of greater and greater degrees of polymerization of the HPLN/Dox on in vivo efficacy with pay-loaded particles, and normal cell toxicity (with non-drug loaded particles). The variations in polymer content are accomplished by varying the molar ratio of h-PEG$_1$-PCDA (polymerizable lipid) to the non-crosslinking lipid component (hydrogenated soy PC). This modification reproducibly controls the amount of polymer that can form in the HPLN. Without wishing to be bound by a particular theory, we think that the diacetylene lipids, being significantly longer in the hydrocarbon tail than the hydrogenated soy PC tails, facilitate a phase separation that results in islands of polymerizable lipids (Gaboriaud 2001). Increasing the relative amount of h-PEG$_1$-PCDA lipid will increase the size and/or number of the polymer domains, per particle. The formulation described herein is held constant except for the molar ratio of h-PEG$_1$-PCDA lipid to hydrogenated soy PC lipid. The drug doxorubicin is actively loaded as before by pH gradient and the new analogs UV polymerized. The degree of polymer formation is checked by absorption at 640 nm. One potential complication we noted earlier was that the higher the level of h-PEG$_1$-PCDA lipid, the lower the level of drug loading that could be established (Federman 2012). We determine the drug loading in each formulation by liposome rupture and the animals are given equivalent amounts of drug in the administration of each formulation. The HPLN/Dox tumor-killing efficacy a function of polymer content is determined first in cell culture and then in vivo, for any promising formulations. In separate experiments, the non-drug loaded analogs are examined in acute toxicity assays to see if increasing levels of polymer lead to any unexpected normal cell toxicity.

Level of PEGylation.

Since the administration method is IV, variations in amount of PEG "stealthing" combined with the targeting ligands may be required to insure a circulation half-life to optimize therapeutic outcome. In general up to a point, increasing surface densities of PEG molecules partially obscures the HPLN surface from recognition by the immune system or by reducing nonspecific RES particle uptake, leading to longer circulation times (John 2003). We test the assumption that longer circulation time will lead to more HPLNs "finding" and sticking to the tumor cells by evaluating the efficacy of the HPLN/Dox formulations as a function of the amount of PEG per particle. The formulation described herein will be held constant except for the relative amount of Peg lipid introduced to the liposome forming mix. After drug loading and any normalization needed due to unequal loading, the targeting agent is be added. As has been noted in the literature, even relatively low levels of PEGylation may significantly retard the insertion of the targeting lipid via the micelle transfer method (Iden 2001). Therefore, the conventional method of inclusion of a maleimide-terminated Peg lipid in the initial liposome forming mix is carried out with the overall Peg content being controlled by increasing the methoxy-terminated PEG component. The efficacy of the anti-CD-19-HPLN/Dox formulations with varying Peg levels is then tested in animals.

Measurement of HPLN zeta potential is critical to improving the formulations. Alterations to the surface of the particle affect the colloidal stability. In general, zeta potentials within a certain range (about +30 to −30 mV) leads to colloidal stability (non-aggregation) and potentials outside that range can result in unwanted flocculation. Determining the zeta potential shortens our HPLN stability testing by reducing the number of candidate formulations and leads to improved shelf life. The zeta potential also indicates the extent of (charged) drug molecules at the particle surface, possibly affecting passive (unwanted) drug release and stability.

Particle Size.

Next, the effects of particle size are examined. Within a limited range of particle sizes, between 50 and 200 nm, removal from circulation through liver filtration or RES sequestration is likely to be minimized. With the fine control over particle size that liposome extrusion offers, we therefore are able to prepare HPLN/drug batches that have a mean particle size centered at 50, 80, 100, and 200 nm. Through prior experience we have seen that the lower size limit for HPLNs are about 30-40 nm. Below this size, the particle curvature is apparently severe enough to impact the lipid packing and the polymerization process is significantly inhibited.

Initially, this size study is conducted on the anti-CD-19/HPLN/Dox formulation. The various sized drug loaded, targeted nanoparticles are analyzed for stability, then administered to animals. Both the efficacy and any unusual toxicities potentially arising from particle size-induced thrombotic events are examined.

As improvements to the other parameters (PEGylation, polymer content, amount of targeting agent, etc.) and type of targeting agent(s) and drug cocktail combinations are identified, the optimal formulations are constructed in the HPLN size range identified empirically here with the longest circulation half-life.

Level of Targeting Agent Optimization.

Finally, the efficacy as a function of the amount of targeting agent is explored. While the levels seen in the literature for nanoparticle in vivo targeting are generally in the 5-10 mole percent range, this parameter must be optimized for the HPLN. Higher targeting protein levels on particles can lead to greater tumor binding while also promoting greater non-specific opsonizing protein sticking.

Initially, this targeting agent amount study is conducted on the anti-CD-19-HPLN/Dox formulation. The conventional method of inclusion of a maleimide-terminated PEG lipid in the initial liposome forming mix is carried out with increasing amounts of mal-lipid. We start with low levels (0.5 mole %) of mal-lipid and create batches with increasingly higher % levels, up to a maximum of about 20-mole %. The efficacy of the anti-CD-19-HPLN/Dox formulations is first assayed first for cell binding in culture, with the formulations showing no or very minimal cell binding discarded. Without wishing to be bound by a particular theory, we anticipate that with increasing targeting agent a binding level plateau will be reached, with perhaps some binding drop-off at the high end. The formulations varying the targeting agent over a range of surface amount, with similar in vitro binding levels are then tested in animals for tumor killing efficacy.

This study is coordinated involving both in vitro and in vivo testing. As these parameters are modified, binding and cell killing are checked through an in vitro study and promising formulations taken on into mice. These optimizations identify a new HPLN formulation with optimized nanoparticle properties for long circulation, maximum cell binding and low toxicity toward normal tissues.

Example 7: Testing of CD-34 Targeted HPLNs in a Xenograft Mouse Model of Human AML Cells Acute myelogenous leukemia (AML) has a particularly poor prognosis and is the most common form in adults. We procure fresh human AML cells from human patients and test them in our NOG mouse model. This study documents similar efficacy in xenografts of patient-derived leukemia cells.

The HPLNs are functionalized first with anti-CD-34 monoclonal antibodies and checked for positive binding to the fresh, human AML cells in vitro. Once binding is demonstrated, the anti-CD-34/HPLNs are drug loaded with doxorubicin (as was done to produce anti-CD19/HPLN/Dox). Initially, efficacy is assessed in vitro using AML cell killing and an LD50 determined. We can also substitute CD-34 affinity peptides for the antibodies, and test the new CD-34 pep/HPLN/Dox for levels of binding and killing of the AML cells. Finally, drug-loaded HPLNs containing cytotoxics that mirror established AML treatment protocols are prepared and tested. NOG mice are injected with fresh human AML cells and tumor cell killing is assessed twice weekly over 8 weeks by performing peripheral blood counts of human AML cells.

Obtaining CD34-Targeted, Drug-Loaded HPLNs:

As described above, either targeting antibodies or engineered peptides toward CD-34 are incorporated into the HPLN membrane by labeled micelle incorporation. Again using the previously described doxorubicin loading methodology, the CD-34 targeted HPLN/Dox particles are obtained. In addition, using the methods described above, a combination of drugs currently being used to treat AML patients are tested in the targeted HPLN formulations. The agents in this cocktail can be mitoxantrone, Ara-C (cytarabine), and VP-16 (etoposide). The loading of drugs into HPLNs is carried out through active loading (doxorubicin) or passive loading, described earlier. The HPLN drug content is again assayed, for doxorubicin as described in Federman 2012, or for the other drugs by particle rupture followed by HPLC quantification.

Assaying CD-34 Targeted HPLN/Drug for Tumor Targeting and Killing:

Fresh AML cells are obtained from human patients and diagnostic flow cytometry (FACS analysis) is again used to demonstrate HPLN binding. Targeting, via either anti-CD-34 antibody or CD-34 peptide, to the AML cells is compared. After optimizing the per-particle level of targeting peptide or antibody, the in vitro tumor killing study is undertaken to validate localization and uptake. In vitro cell killing is analyzed by the CellTiter-Glo Luminescent Cell Viability Assay (RLU).

After the CD-34 targeted HPLN is optimized in vitro, the in vivo tumorcidal activity assay in mice is performed. As carried out before with ALL cells, NOG mice are be injected with $6 \times 10^6$ AML cells. The systemic distribution and cell killing by CD-34 targeted HPLN/drug are assessed twice weekly by peripheral blood cell counts of human AML cells. Upon completion of the treatment regimen, necropsies are performed to assess and quantitate any residual disease in liver, spleen, bone marrow, and CNS.

This study leads to the successful demonstration that a CD-34 targeted HPLN that can bind to and kill AML leukemia cells in a xenograft mouse model, and provides a new formulation comprised of a drug-loaded, CD-34 targeted HPLN that functions in vivo with tumorcidal activity.

Figure 10:
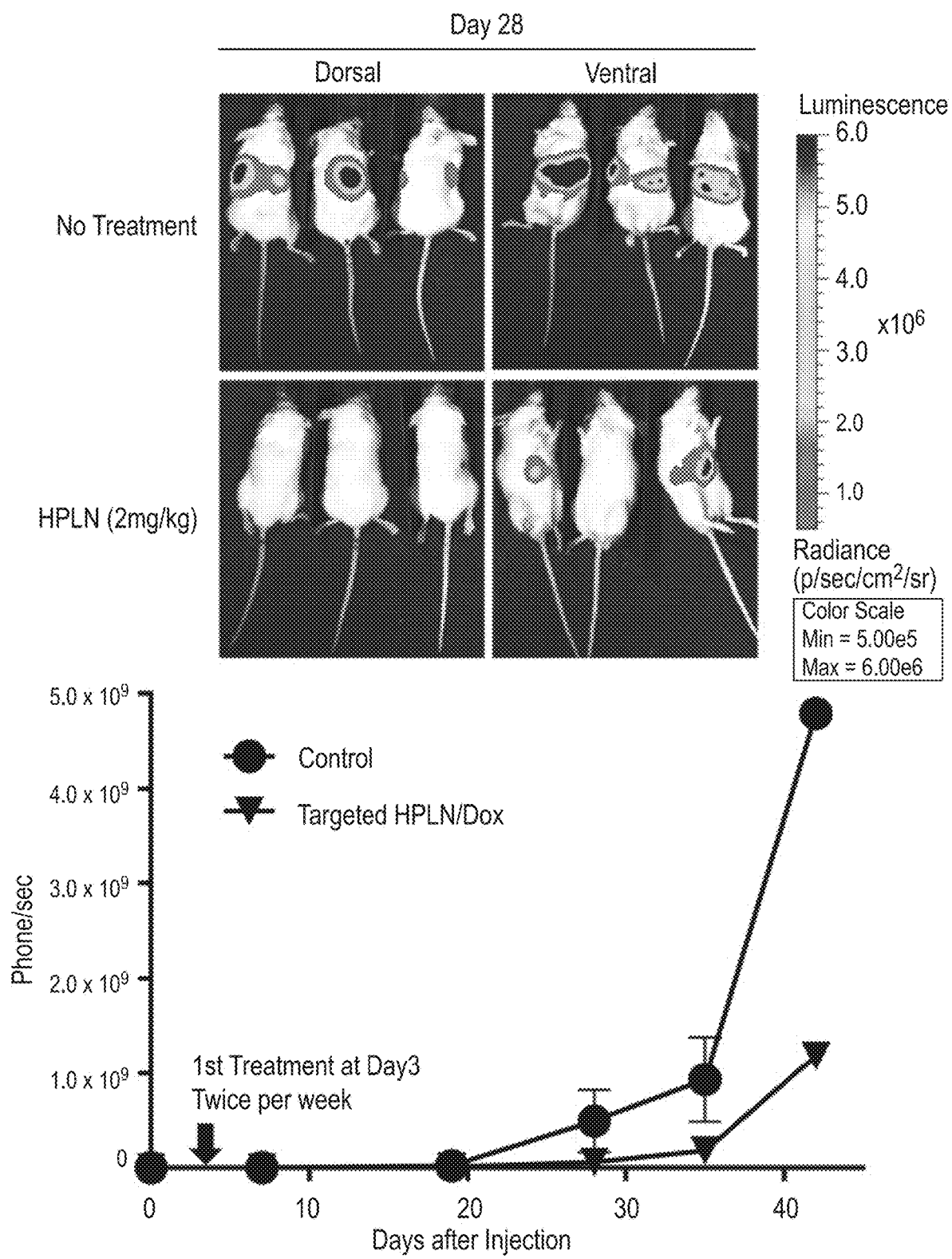
FIG. 10 depicts, in accordance with various embodiments of the invention, the efficacy response of anti-CD99-HPLN/Dox administered to a metastatic xenograft mouse model of Ewing tumor made by tail vein injection of TC71-Luc cells. Metastatic tumor burden was estimated from Xenogen camera images. The mice were treated with anti-CD99-HPLN by IV administration containing 2 mg/kg Doxorubicin twice per week. Tumor images (Top panel) were made from both of dorsal and ventral side after the injection of luciferin once a week. The total tumor burden was calculated from the summation of both sides and plotted in the bottom panel.
Figure 12:
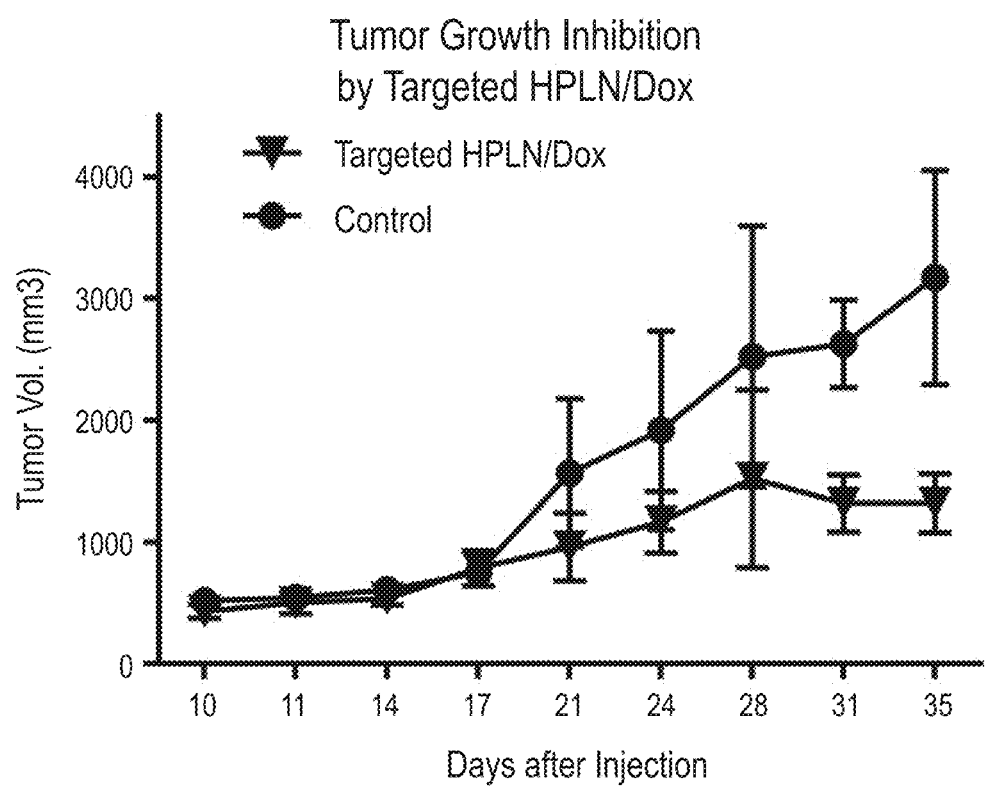
FIG. 12 depicts, in accordance with various embodiments of the invention, the efficacy response of a subcutaneous TC71 xenograft mouse model of Ewing sarcoma treated with anti-CD-99-HPLN/Dox by IV administration containing 2 mg/kg Doxorubicin twice per week starting at day 10. Tumor burden was measured using a handheld caliper at the indicated days.
Figure 13:
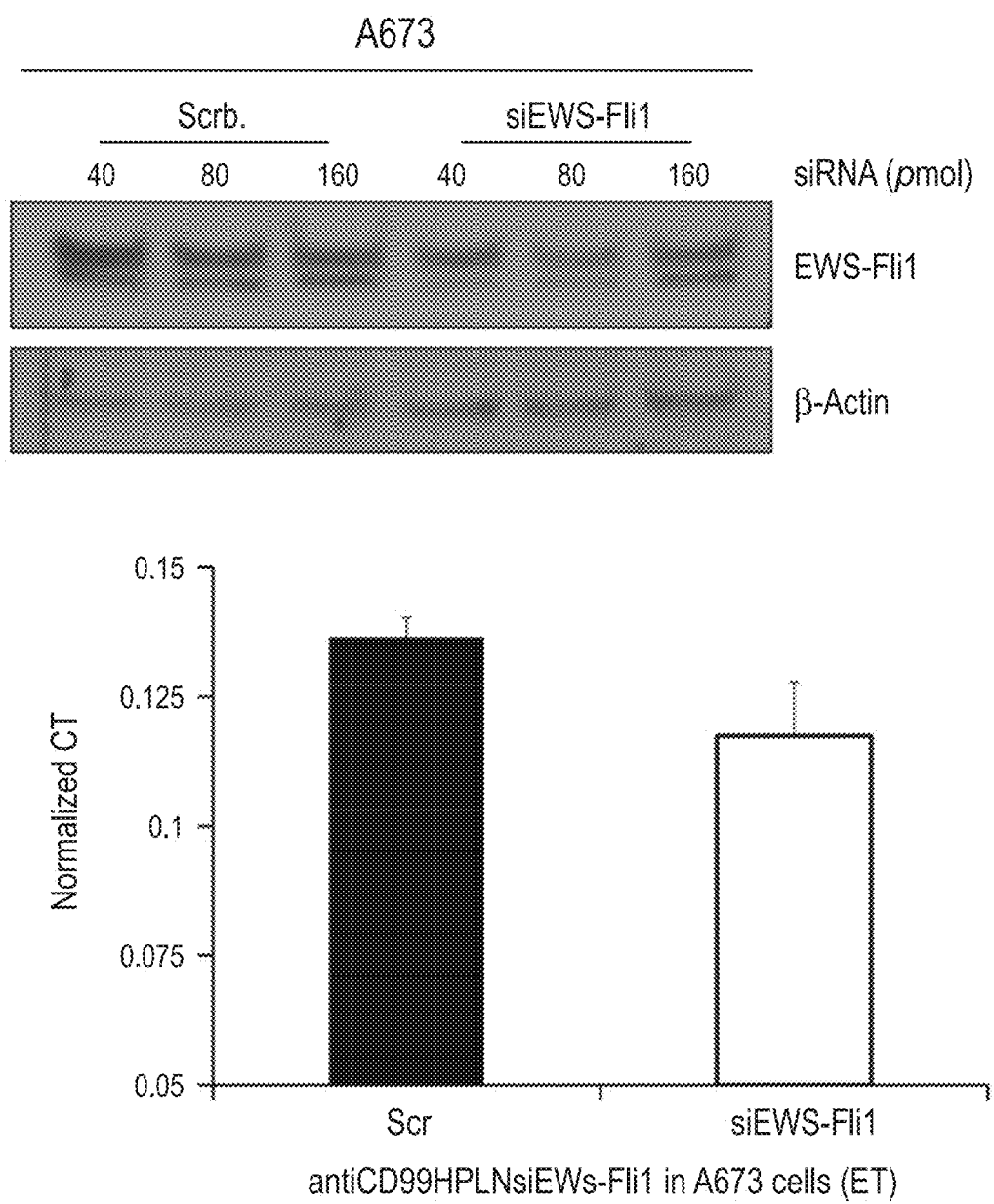
FIG. 13 depicts, in accordance with various embodiments of the invention, that HPLN containing siRNA against EWS-Fli1 can knockdown EWS-Fli1 in A673 Ewing tumor cells. Top panel depicts western blots showing the knockdown of EWS-Fli and bottom panel depicts QRT PCR showing the reduced expression of EWS-Fli1.

Example 8: Testing of CD-99 Targeted HPLNs in a Xenograft Mouse Model of Human Ewing Sarcoma We tested the efficacy HPLNs loaded with doxorubicin and targeted with antibodies toward CD-99 (anti-CD-99/HPLN/Dox) in NOG mice. In the subcutaneous model, luciferase-transfected Ewing tumors were implanted in six mice. Three mice received buffer solution; three mice received anti-CD-99/HPLN/dox (2 mg/kg dox, twice per week). Drug administration was started at time point ten days after implantation and tumor size was estimated by caliper measurements (FIG. 12). In the metastatic model, six mice were injected with $5 \times 10^6$ TC71-Luc Ewing tumor cells through the tail vein and drug administration was started three days after implantation. Three mice received anti-CD-99/HPLN/dox (2 mg/kg dox, twice per week) and three mice received only vehicle (FIG. 10). Tumor size was estimated by Xenogen camera images.

Figure 11:
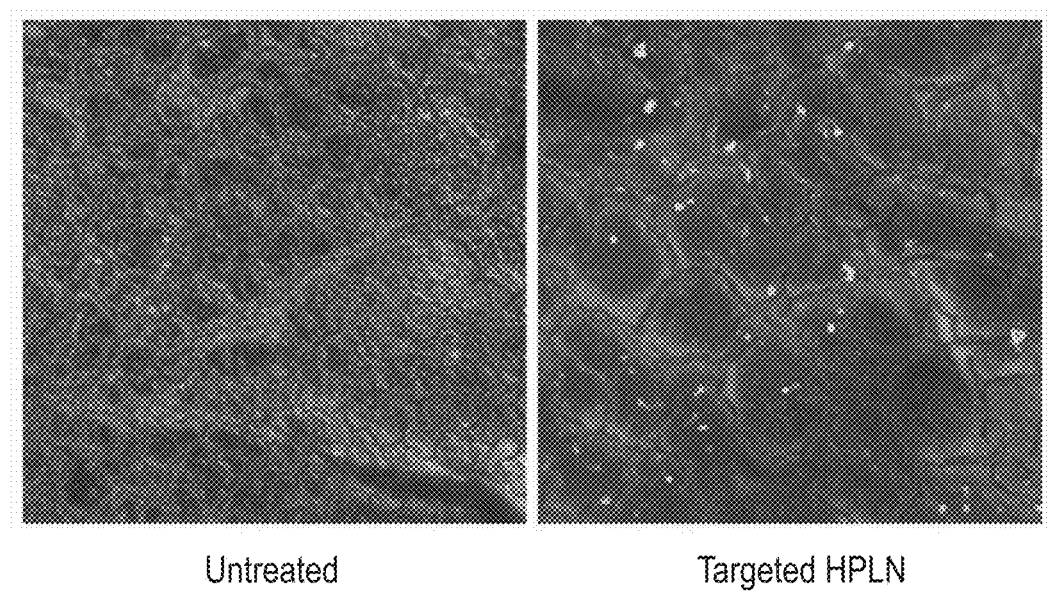
FIG. 11 depicts, in accordance with various embodiments of the invention, that xenografted Ewing TC71 tumors treated with CD-99 targeted HPLNs showing localization of HPLNs (white) in excised tumor tissue.

Efficacy Results:

The drug-loaded HPLNs were very well tolerated in the mice, as there were no acute toxic reactions observed. In prior studies, we have shown that HPLN did not have an adverse effect on the animals: body mass matched that of controls, and liver, kidney, and bone marrow function studies remained normal. The mice receiving anti-CD-99/HPLN/Dox however showed a significant retardation in tumor growth. At day 24, in the subcutaneous model there was almost a 2.5 fold difference for the targeted HPLN treated animals, compared to the untreated controls (FIG. 12). The tumor growth in the untreated control mouse was very large by day 24, and animal care protocol required it to be euthanized. Especially encouraging, was the observed tumor growth curve in the HPLN treated mice. Tumor growth has apparently plateaued about 20 days after treatment started. The metastatic model also showed significant tumor burden reduction compared to the control. By day 35, this is estimated to be about a 4.5 fold reduction in tumor size (FIG. 10). Xenogen pictures dramatically show the difference in tumor size between the treated and control animals (FIG. 10). Excised tumors from HPLN treated mice showed the strong presence of HPLN localization (FIG. 11).

Example 9: General Assay Methodology

The testing of the new HPLNs is carried out by first testing the formulations in cell-based binding and cytotoxicity assays. The most promising analogs are administered to mice bearing human ALL or AML, cells for tumor binding, internalization and killing studies.

Cell-Based Testing.

First, where specific changes to the cell targeting or PEGylation components are conducted, the level of tumor cell binding is be measured. The visualization of HPLNs attached to cells is possible because of the inherent fluorescent property imparted by the diacetylenic polymer backbone (Hendrikx 2005). The quantification of binding is done by measuring the fluorescent signal in the rhodamine channel of a FACScan flow cytometer. The binding is expressed as a relative percentage compared to a positive control, targeted-HPLNs, and the negative untreated cells.

Cell Binding Assay.

Leukemia cell lines are seeded onto 4-well Lab-Tek II Chamber Slides (Thermo Scientific) to reach 80% confluence overnight. Cells are treated with targeted HPLNs at 50 µg/mL per well and incubated for 4 hrs at 37° C. Media is removed, and wells are washed with 1 mL fresh media. Cell fixation is done with 3.7% formaldehyde in Phosphate buffered saline for 15 minutes at 4° C. Cells are mounted using VECTASHIELD mounting medium with DAPI (Vector Laboratories) and then viewed using a Carl Zeiss Axio Imager D1 fluorescence microscope. DAPI is used to visualize the cell through blue/cyan filter and bound HPLNs are visualized using the rhodamine filter at a 1 second exposure. Alternatively, the binding can be quantified with a FACScan flow cytometer (Becton Dickinson, San Jose, Calif.). Prior to fixing the cells, the plates are gently agitated to detach the cells and the solution injected into the FACS. HPLN quantification is done be measuring the signal through the rhodamine filter.

MTT Cytotoxicity Assay.

The leukemia cell lines are suspended in Dulbecco's Modified Eagle Medium (HyClone Cat no. SH30022.01) with 10% fetal bovine serum (Gemini Bioproducts). Cells are seeded in a 96-well format at a concentration of 5 Å~$10^3$ cells/well at a volume of 100 µL media with penicillin/streptomycin and incubated overnight. The following day, wells are treated with targeted HPLN/drug, untargeted HPLNs, conventional liposomes, or free drug for a four-hour period then washed with fresh media. Doses are added based on drug concentrations ranging on a log scale from 0.01 to 100 µM and at 0 nM. The 0 nM well is treated with HEPES-buffered saline. Each treatment ise performed in triplicate. Cells are incubated under standard CO2 conditions for 72 hrs at 37° C. At 72 hrs, all wells will be treated with 10 µL of thiazolyl blue tetrazolium bromide (Sigma) solution at an initial concentration of 5 µg/µL in phosphate buffered saline and incubated for 4 hrs. Reaction ceases and the cells are lysed by adding 100 µL of 15% sodium dodecyl sulfate/15 mM HCl solution and incubated overnight in the dark at room temperature. Plate absorbance is read using a Bio-Rad microplate reader at 570 nm.

Apoptosis Assay.

After drug treatments (IC80 for each drug), both floating and attached cells are collected and subjected to annexin V/PI staining using annexin V-FITC Apoptosis Detection Kit (Oncogene Research Products, San Diego, Calif.) according to the protocol provided by the manufacture. In cells undergoing apoptosis, annexin V binds to phosphatidylserine, which is translocated from inner to outer leaflet of the cytoplasmic membrane. PI is used to distinguish between viable, early apoptotic and necrotic or late apoptotic cells. The resulting fluorescence from HPLN treated and untreated cells is measured by flow cytometry using a FACScan flow cytometer.

Animal Testing.

To address the limitations of in vitro assays, murine xenograft models have been developed to allow engraftment of primary patient samples and cell lines. Xenograft models of freshly engrafted human cancer cells have the unique advantage of being able to explore human cell-specific biology in vivo, and are generally thought to better mimic patient response. In this model we transplant freshly obtained human cancer cells into the immunodeficient mice, providing the opportunity to test new HPLN formulations in vivo.

NOG Mouse Testing.

We and others have found that the typical non-obese diabetic (NOD)/SCID mice have the remnant NK cell activity that rejects the engraftment of human leukemia cancer cells. To address this, a further immune-compromisation has been established with NOD-SCID mice, which have deletions in the gene encoding the interleukin 2-receptor γ (IL2Rγ). In addition, these mice have added genes expressing human iL3, GM-CSF and SCF. These mice (NOG) now have a complete lack of B, T, and NK cells, and a deficiency of cytokine signaling. We have observed in the testing that the NOG mice have a higher xenograft success rate, prolonged survival and higher metastasis rate of injected cancer cells compared to the NOD/SCID mice. They provide a superior model for the longer-term studies.

In addition to testing the HPLN formulations against the ALL cell line we used, further testing is done with AML cells freshly isolated from patients. The luciferase-transfected ALL tumor cells when injected into NOG mice create a mouse xenograft model of leukemia with systemic distribution and allow cell killing by targeted HPLNs to be assessed by Xenogen camera imaging. With AML cells, since these are freshly isolated cells and luciferase transfection is not feasible, tumor killing and induction of remission will be assessed as in patients, by peripheral blood counts.

The specific protocol is as follows: 0.5 ml of whole blood will be drawn from the tail vein into pediatric sized purple top tubes and sent to the clinical laboratory. An automated heme analyzer provides total red and white cell counts, and an automated differential count of wbc's and lymphocytes. Myeloid blast counts are automatically generated, but are manually confirmed by microscopic analysis and counting of peripheral blood smears prepared from the same blood draw, precisely as performed on leukemia patient material. Bone marrow involvement cannot be reasonably determined on living animals due to size limitations, but is documented (as well as liver, spleen, and CNS involvement) at the time of necropsy.

Mice are treated according to the NIH Guidelines for Animal Care and as approved by the CHLA or USC Institutional Animal Care and Use Committee. Athymic male nude (NOG) mice will be used for in vivo testing experiments and BALb/c nude (nu/nu) mice will be used for PK studies. The animals are fed ad libitum and kept in air-conditioned rooms at 20±2° C. with a 12 h light-dark period. All mice are 6-8 weeks of age at the time of injection. Each mouse is injected with $6 \times 10^6$ transfected leukemia cells suspended in 0.2 mL RPMI (without FBS or antibiotics) through the tail vein using a 27-gauge needle. All experimental manipulations with the mice are performed under sterile conditions in a laminar flow hood.

Maximum Tolerable Dose.

MTD is an acceptable and well-established toxicity-based endpoint assay. The highest dose of drug that can safely be given is determined in an unblinded, dose-escalation experiment examining its toxicity and tolerability in mice. Since the pharmacokinetic parameters of free (unencapsulated) drug and nanoparticle-encapsulated forms are likely to be very different, traditional toxicity/tolerability comparisons may not be applicable. As the strength of this technology comes from targeted delivery, an easily measured parameter such as bone marrow toxicity will be chosen for initial assessment. Doses (1 mg/kg to 20 mg/kg) will be given to 5 groups of mice (n=6) using IV infusion. A power analysis indicates that a minimum of 5 mice per group is needed. If dose-limiting toxicity (DLT) is not observed the dose will be escalated until the MTD is established. The MTD is defined as one dose below that which resulted in DLT in any two mice within a group. Blood and various organs including, kidney, liver, heart, lung, ovary, intestine, as well as bone marrow will be collected for histopathology. Animals given the MTD of these HPLN-encapsulated compounds are compared to an administration of the free drug at its MTD with respect to a single-dose administration that produces sustained, dose-related inhibition of tumor growth for all the studies in the adult leukemia model, described above.

Metronomic Dosing.

Traditionally cancer chemotherapeutic agents are given with closely spaced bolus infusions of drugs at or near the MTD, followed by substantial rest periods. The typical results were transitory improvements in tumor burden and lifespan extension accompanied by disturbing side effects and eventual relapse. The new metronomic scheduling involves dosing at constant intervals without rest periods (Hanahan 2000). The use of lower doses in theory should minimize toxic side effects. The metronomic and combinatorial dosing strategies can kill tumor endothelial cells as well as overt cancer cells and, perhaps, other cellular constituents of a tumor, offering the prospect for genuine efficacy. True efficacy may come only with combinatorial therapies, wherein novel cytotoxic dosing schedules are used in conjunction with other drugs or radiation. After establishing the best route of administration and MTD we use very low dose metronomic scheduling to compare the in vivo efficacy of these compounds as single agents and in combination. Doses (0.2 mg/kg to 3 mg/kg) are given to five groups of mice (n=6) for the duration of the experiment (60 days) as determined previously. These compounds are administered to 4 mice at doses of 0, 4, 10, and 20 mg/kg/day. Following 7-days of dosing, plasma samples are collected at 0, 0.5, 1, 2, 4, 8, 12 and 24 hours post dose. Plasma concentrations are monitored using LC/MS/MS. Noncompartmental analysis is used to determine AUC, t½, Cmax, Tmax, CL, and % F.

Statistical Analysis.

Assays are set up in triplicates and the results are expressed as means±SD. Statistical analysis and P-value determination is done by two-tailed paired t-test with a confidence interval of 95% for determination of the significance differences between treatment groups. P<0.05 is considered to be significant. ANOVA is used to test for significance among groups. The SAS statistical software package (SAS Institute) is used for statistical analysis.

In a xenograft model, cancer cells are not exposed to a competent immune system. Testing in a mouse with a competent immune system can be done through treatment of a wild type mouse by a chemical carcinogen/radiation or by oncogene delivery/insertional mutagenesis. There are several methods to make these transgenic mice for the study of leukemogenesis and response to the various therapies (Zuber 2009). We can generate mice containing leukemia using these known methods.

REFERENCES

1. Federman, N J, Chan, J, Nagy, J O, Landaw, E M, McCabe, K, Wu, A M, Triche, T, Kang, H, Liu, B, Marks, J D, Denny, C T (2012) Enhanced Growth Inhibition of Osteosarcoma by Cytotoxic Polymerized Liposomal Nanoparticles Targeting the Alcam Cell Surface Receptor Sarcoma 2012:126909.
2. Haran G, Cohen R, Bar L K, Barenholz Y, (1993) Transmembrane ammonium sulfate gradients in liposomes produce efficient and stable entrapment of amphipathic weak bases. Biochimica et Biophysica Acta, 1151: 201.
3. Iden D L, Allen T M (2001) In vitro and in vivo comparison of immunoliposomes made by conventional coupling techniques with those made by a new post-insertion approach Biochimica et Biophysica Acta 1513: 207-216.
4. Almagro, J C, Fransson, J (2008) Humanization of Antibodies. Frontiers in Bioscience, 13:1619-1633
5. Zucker D, Barenholz Y. (2010) Optimization of vincristine-topotecan combination—paving the way for improved chemotherapy regimens by nanoliposomes. J Control Release. 146(3):326-33.
6. Gaboriaud, F, Golan, R, Volinsky, R, Berman, A, Jelinek, R (2001) Organizational and Structural Properties Langmuir Films Composed of Conjugated Polydiacetylene and Phospholipids. Langmuir 17:3651-3657.
7. John, A E, Lukacs, N W, Berlin, A A, Palecanda, A, Bargatze, R F, Stoolman, L M, Nagy, J O (2003) Discovery of a potent nanoparticle P-selectin antagonist with anti-inflammatory effects in allergic airway disease. Faseb J 17:2296-2298.
8. Hendrikx, C C, Polhuis, M, Pul-Hootsen, A, Koehorst, R B, van Hoek, A, Zuilhof, H, Sudholter, E J (2005) Spectroscopic studies of oligodiacetylenes in solution and polymer film. Phys Chem Chem Phys 7:548-553.

9. Hanahan, D, Bergers, G, Bergsland, E (2000) Less is more, regularly: metronomic dosing of cytotoxic drugs can target tumor angiogenesis in mice. J Clin Invest 105:1045-1047.
10. Zuber J, Radtke I, Pardee T S, Zhao Z, Rappaport A R, Luo W, McCurrach M E, Yang M M, Dolan M E, Kogan S C, Downing J R, Lowe S W. (2009) Mouse models of human AML accurately predict chemotherapy response. Genes & Development, 23:877-889.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A hybrid polymerized liposomal nanoparticle, comprising:
   a polymerizable lipid, wherein the polymerizable lipid comprises at least one PEGylated polymerizable lipid having a PEG polymer chain, wherein the PEGylated polymerizable lipid having the PEG polymer chain is m-PEG2000-PCDA, and wherein the hybrid polymerized liposomal nanoparticle is a non-aggregating hybrid polymerized liposomal nanoparticle; and
   a non-polymerizable lipid.

2. A method of loading a therapeutic agent into a hybrid polymerized liposomal nanoparticle, comprising:
   providing a hybrid polymerized liposomal nanoparticle of claim 1, wherein the hybrid polymerized liposomal nanoparticle comprises a polymerizable lipid and a non-polymerizable lipid, wherein the polymerizable lipid comprises at least one PEGylated polymerizable lipid having a PEG polymer chain, wherein the PEGylated polymerizable lipid having the PEG polymer chain is m-PEG2000-PCDA, and wherein the hybrid polymerized liposomal nanoparticle is a non-aggregating hybrid polymerized liposomal nanoparticle;

establishing an ion gradient across a membrane of the hybrid polymerized liposomal nanoparticle;

providing a therapeutic agent; and incubating the therapeutic agent with the hybrid polymerized liposomal nanoparticle, thereby loading the therapeutic agent into the hybrid polymerized liposomal nanoparticle.

3. The method of claim 2, wherein the ion gradient is an ammonium sulfate gradient and/or pH gradient.

4. The method of claim 2, wherein a concentration of the PEGylated polymerizable lipid having the PEG polymer chain is about 0.1-1, 1-5, 5-10, or 10-15 mol % of the hybrid polymerized liposomal nanoparticle.

5. The method of claim 2, wherein the therapeutic agent is doxorubicin, irinotecan, cis-platin, topotecan, vincristine, mytomicin, paclitaxel, cytarabine, mitoxantrone, Ara-C (cytarabine), VP-16 (etoposide), or siRNA, or a combination thereof.

6. A method of conjugating a targeting agent to a hybrid polymerized liposomal nanoparticle, comprising:

providing a lipid micelle;

providing a targeting agent;

conjugating the targeting agent to the lipid micelle;

providing a hybrid polymerized liposomal nanoparticle of claim 1, wherein the hybrid polymerized liposomal nanoparticle comprises a polymerizable lipid and a non-polymerizable lipid, wherein the polymerizable lipid comprises at least one PEGylated polymerizable lipid having a PEG polymer chain, wherein the PEGylated polymerizable lipid having the PEG polymer chain is m-PEG2000-PCDA, and wherein the hybrid polymerized liposomal nanoparticle is a non-aggregating hybrid polymerized liposomal nanoparticle; and incubating the hybrid polymerized liposomal nanoparticle with the lipid micelle conjugated with the target agent, thereby transferring the targeting agent to the hybrid polymerized liposomal nanoparticle.

7. The method of claim 6, wherein the targeting agent is an anti-CD19 antibody, anti-CD34 antibody, anti-CD99 antibody, anti-CD117 antibody, anti-CD166 antibody, or anti-CA19-9 antibody, or a combination thereof.

8. The method of claim 6, wherein the targeting agent is a peptide capable of specifically binding to a surface marker on a cancerous cell.

9. The method of claim 6, wherein the targeting agent is conjugated to the lipid micelle through a reaction between a thiol group on the targeting agent and a maleimide group on the lipid micelle.

10. The method of claim 6, wherein a concentration of the PEGylated polymerizable lipid having the PEG polymer chain is about 0.1-1, 1-5, 5-10, or 10-15 mol % of the hybrid polymerized liposomal nanoparticle.

11. A method of conjugating a targeting agent to a hybrid polymerized liposomal nanoparticle, comprising:

providing a targeting agent with a free thiol group;

providing a hybrid polymerized liposomal nanoparticle of claim 1, wherein the hybrid polymerized liposomal nanoparticle comprises a polymerizable lipid and a non-polymerizable lipid, wherein the polymerizable lipid comprises at least one PEGylated polymerizable lipid having a PEG polymer chain, and at least one maleimide terminated PEGylated lipid, wherein the PEGylated polymerizable lipid having the PEG polymer chain is m-PEG2000-PCDA, and wherein the hybrid polymerized liposomal nanoparticle is a non-aggregating hybrid polymerized liposomal nanoparticle; and incubating the hybrid polymerized liposomal nanoparticle with the target agent containing the free thiol, thereby covalently conjugating the targeting agent to the hybrid polymerized liposomal nanoparticle.

12. The method of claim 11, wherein the targeting agent is an anti-CD19 antibody, anti-CD34 antibody, anti-CD99 antibody, anti-CD117 antibody, anti-CD166 antibody, or anti-CA19-9 antibody, or a combination thereof.

13. The method of claim 11, wherein the targeting agent is a peptide capable of specifically binding to a surface marker on a cancerous cell.

14. The method of claim 11, wherein the targeting agent is conjugated to a polymerized liposome outer surface through a reaction between a thiol group on the targeting agent and a maleimide group on the polymerized liposome outer surface.

15. The method of claim 11, wherein a concentration of the PEGylated polymerizable lipid having the PEG polymer chain is about 0.1-1, 1-5, 5-10, or 10-15 mol % of the hybrid polymerized liposomal nanoparticle.

* * * * *